(12) United States Patent
Thayumanavan

(10) Patent No.: US 7,687,600 B2
(45) Date of Patent: Mar. 30, 2010

(54) INVERTIBLE AMPHIPHILIC POLYMERS

(75) Inventor: Sankaran Thayumanavan, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/184,324

(22) Filed: Jul. 19, 2005

(65) Prior Publication Data

US 2007/0293669 A1 Dec. 20, 2007

Related U.S. Application Data

(60) Provisional application No. 60/588,938, filed on Jul. 19, 2004.

(51) Int. Cl.
*C08G 64/00* (2006.01)
*C08F 6/00* (2006.01)

(52) U.S. Cl. .................. 528/480; 514/255.03; 514/300; 514/301; 514/302; 544/235; 544/236

(58) Field of Classification Search ............ 514/255.03, 514/300, 301, 302; 528/480; 544/235, 236
See application file for complete search history.

(56) References Cited

U.S. PATENT DOCUMENTS

| | | | |
|---|---|---|---|
| 6,265,428 B1 * | 7/2001 | Chan et al. ................... | 514/396 |
| 2003/0125281 A1 * | 7/2003 | Lewis et al. .................... | 514/44 |
| 2003/0144458 A1 | 7/2003 | Watterson et al. | |

FOREIGN PATENT DOCUMENTS

| | | |
|---|---|---|
| JP | 57171947 * | 10/1982 |
| JP | 57171947 B | 10/1982 |
| WO | WO 02/077037 A2 | 10/2002 |

OTHER PUBLICATIONS

Basu, S; Vutukuri DR; Shyamroy, S; Sandanaraj, BS and Thayumanavan, S; Supporting Information for: Invertible Amphiphilic Homopolymers; Department of chemistry, University of Massachusetts, Amherst, MA.
Basu, S; Vutukuri, D; Shyamroy, S; Sandanaraj, BS; and Thayumanavan, S; Invertible Amphiphilic Polymers; Department of Chemistry, University of Massachusetts, Amherst, MA,(Advance copy later published, J. Am. Chem. Soc. 2004, 9890-9891, 126.
Basu, S; Vutukuri, DR; Shyamroy, S; Sandanaraj, BS; and Thayumanavan, S; Invertible Amphiphilic Homopolymers; J. Am. Chem. Soc., 2004, 9890-9891, vol. 126.
Sandanaraj, BS; Vutukuri, DR; Simard, JM; Klaikherd, A; Hong, R; Rotello, VM; and Thayumanavan, S; Noncovalent Modification of Chymotrypsin Surface Using an Amphiphilic Polymer Scoffold: Implications in Modulating Protein Function; J. Am. Chem. Soc.; 2005, 10693-10698, vol. 127.
Arumugam, S; Vutukuri, DR; Thayumanavan, S; and Ramamurthy, V; Amphiphilic Homopolymer as a Reaction Medium in Water: Product Selectivity within Polymeric Nanopockets, J. Am. Chem. Soc., 2005, 13200-13206, vol. 127.
Basu, S; Vutukuri, DR; and Thayumanavan, S; Homopolymer Miceiles in Heterogeneous Solvent Mixtures, J. Am. Chem. Soc., 2005, 16794-16795, vol. 127.
Sandanaraj, BS; Demont, R; Aathimanikandan, SV; Savariar, EN; and Thayumanavan, S; Selective Sensing of Metalloproteins From Nonselective Binding Using a Fluorogenic Amphiphilic Polymer; J. Am. Chem. Soc., 2006, 10686-10687, vol. 128.
Savariar, EN; Aathimanikandan, SV and Thayumanavan, S; Supramolecular Assemblies from Amphiphilic Homopolymers: Testing the Scope; J. Am. Chem. Soc., 2006, 16224-16230, vol. 128.
Arumugam, S; Vutukuri, DR; Thayumanavan, S; and Ramamurthy, V; A Styrene Based Water Soluble Polymer as a Reaction Medium for Photodimerization of Aromatic Hydrocarbons in Water; Journal of Photochemistry and Photobiology A: Chemistry, 2007, 168-171, vol. 185.
Julthonpiput: "Y-shaped Amphiphilic Brushes with Switchable Micellar Surface Structures" Journal of the American Chemical Society, vol. 125, Nov. 26, 2003, p. 15912-15921.
Basu et al.: "Invertible Amphiphilic Homopolymers" Journal of the American Chemical Society, vol. 126, Jul. 24, 2004, pp. 9890-9891, XP002465169.

* cited by examiner

*Primary Examiner*—Terressa M Boykin
(74) *Attorney, Agent, or Firm*—Reinhart Boerner Van Deuren s.c.

(57) ABSTRACT

Amphiphilic monomeric compounds and corresponding homopolymers and copolymers capable of assembly and invertible configuration in introduction to and change in fluid medium.

21 Claims, 7 Drawing Sheets

1a; R = H
1b; R = Br

2a; R = H
2b; R = Br (M = H, Na, K, Cs)
3a; R = H
3b; R = Br

Examples of Structure I

Examples of Structure II

Examples of Structure III

Examples of Structure IV

Figure 4
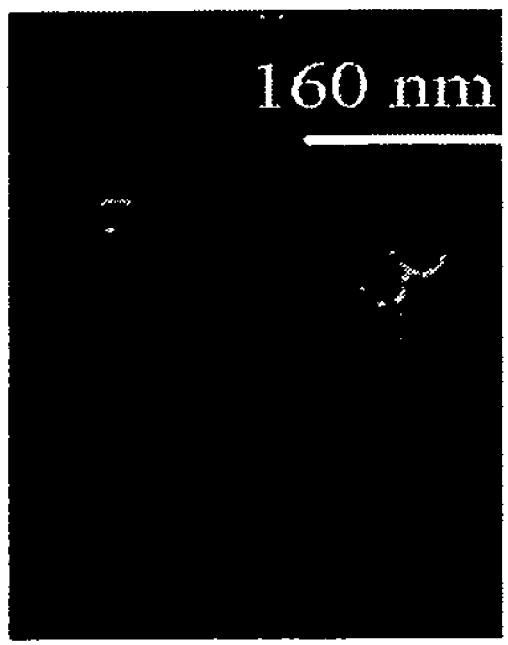
S1
Figure 4A
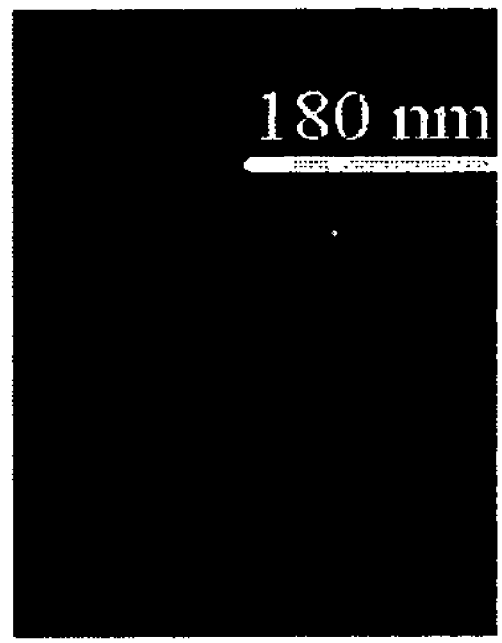
S2
Figure 4B

Figure 5
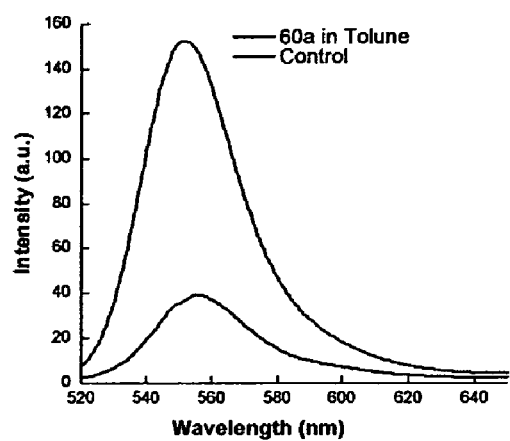
Fig. 5A
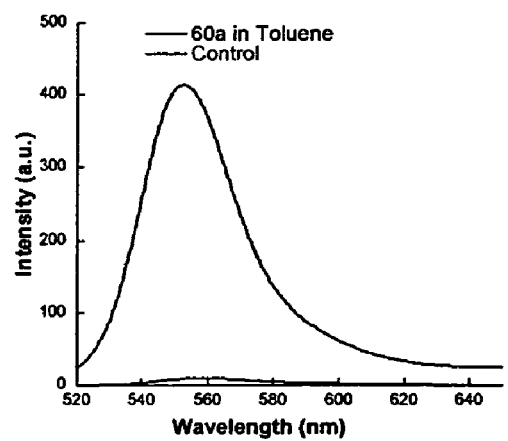
Fig. 5B

INVERTIBLE AMPHIPHILIC POLYMERS

This application claims priority from application Ser. No. 60/588,938 filed Jul. 19, 2004, the entirely of which is incorporated herein by reference.

Self-organization of amphiphilic polymers has resulted in assemblies such as micelles, vesicles, fibers, helical superstructures, and macroscopic tubes. These nanoscale to macroscale morphologies are already of interest in areas ranging from material science to biology. Stimuli-responsive versions of these assemblies are likely to further enhance their scope as "smart" materials. Thermo- or pH-sensitive polymer micelles and vesicles have been reported in which the nature of the functionality at the corona changes in response to the stimulus. To-date, little attention has been paid to realize an environment-dependent switch from a micelle-type assembly with a hydrophilic corona to an inverted micelle-type assembly with a lipophilic corona. Block copolymers are often the choice for a wide variety of assemblies, in which the fundamental driving force involves the mutual immiscibility of the blocks and/or the immiscibility of one of the blocks in the bulk solvent. For example, poly(styrene-co-acrylic acid) block copolymers exhibit several interesting amphiphilic assemblies. These self-assembled structures are the result of the incompatibility between the hydrophobic polystyrene block and the hydrophilic polyacrylic acid block.

Amphiphilic polymers with rigid polymer backbones have been reported. However, such compounds are not capable of providing micelle and inverse-micelle type nanostructures. While small molecule surfactants are known to form invertible structures, they exhibit large critical micelle concentrations; that is, the concentration at which the molecule exhibits micellar properties. High concentrations of such difunctional compounds, in turn, tend to induce unwanted phase separation.

BRIEF DESCRIPTION OF THE DRAWINGS

FIGS. 4A-B. TEM images showing the structural integrity of the micelle-like A) and inverted micelle-like (B) particles at concentrations of $10^{-9}$M.

FIGS. 5A-B. With reference to example 18, emission spectra of R6G with polymer 60a in toluene. A) 60a in toluene without base, compared to the dye in water as control. B) 60a in toluene with one equivalent of KOH, compared with an aqueous solution of R6G containing potassium acetate as control.

SUMMARY OF THE INVENTION

Figure 1:
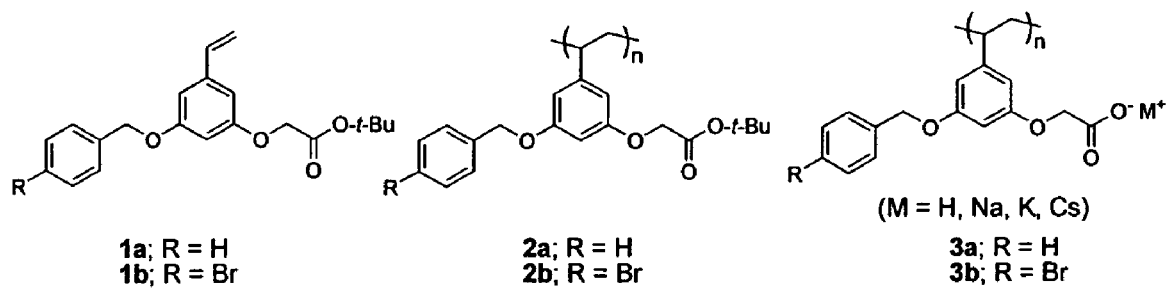
FIG. 1. Representative monomers and polymers of certain embodiments, in accordance with certain aspects of this invention.
Figure 2A:
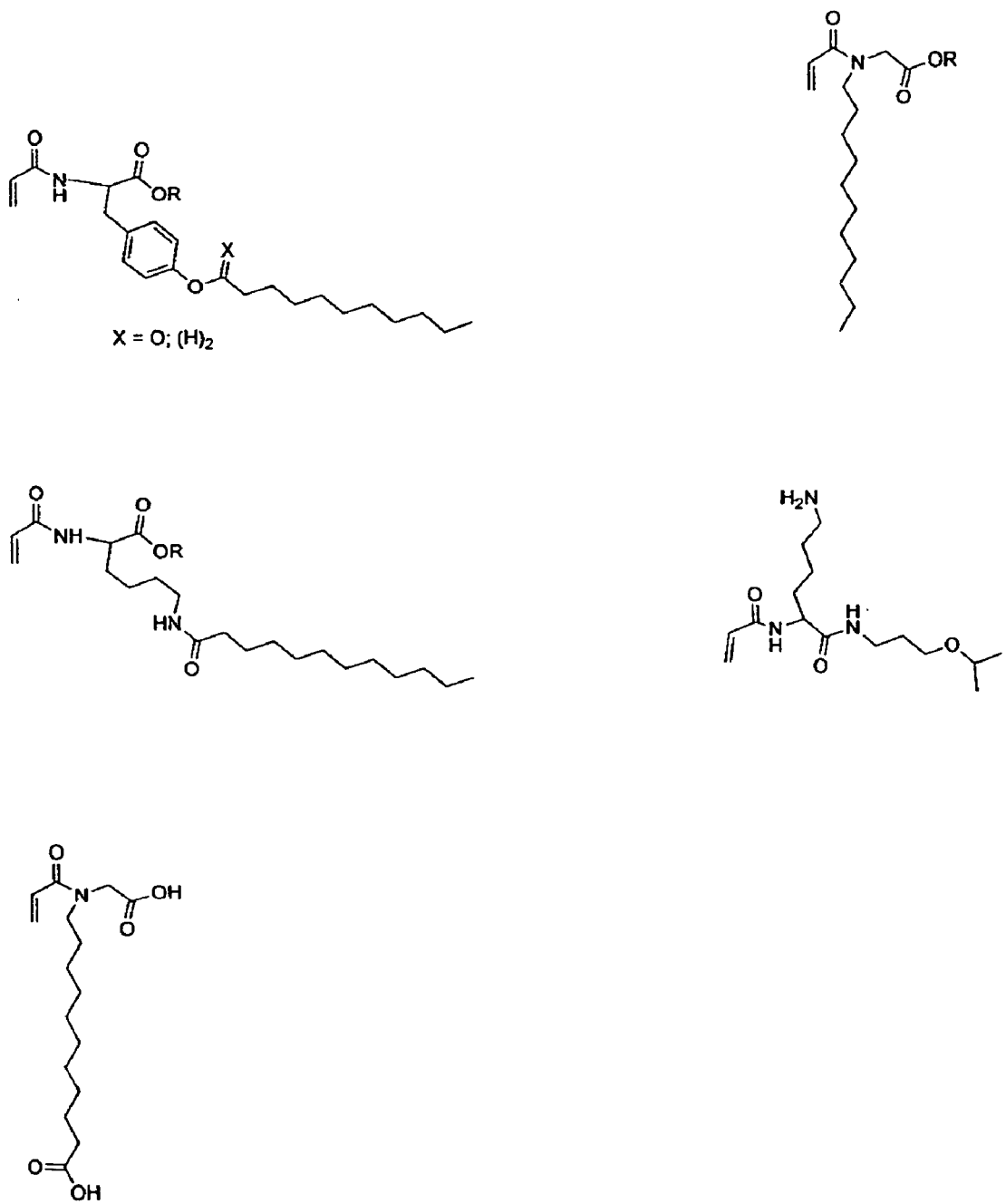
FIG. 2A. Representative acrylate monomeric compounds of this invention, in accordance with certain aspects thereof, showing various hydrophilic and hydrophobic moieties; in particular where an alkyl amine group can be used to impart hydrophilicity and/or antimicrobial properties in the form of an acid salt, and where a carboxy-terminated N-alkyl moiety can be used to provide two hydrophilic moieties coupled by a hydrophobic (i.e., alkyl) moiety, polymers of which can be used to form vesicles.
Figure 2B:
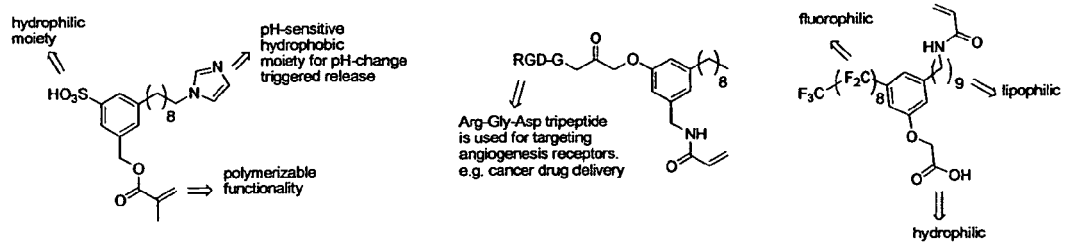
FIG. 2B. Additional representative compounds of this invention, in accordance with certain aspects thereof.
Figure 2B:
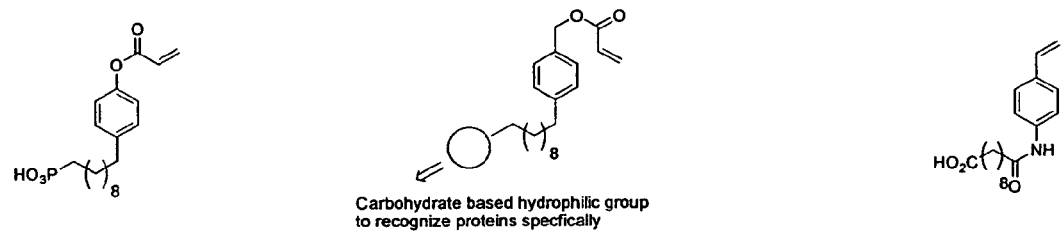
Figure 2B:
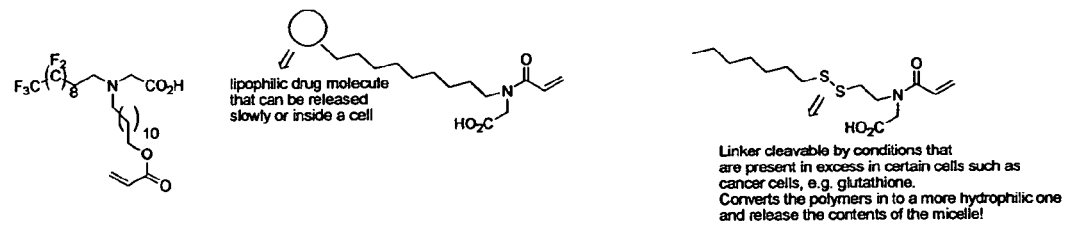
Figure 2B:
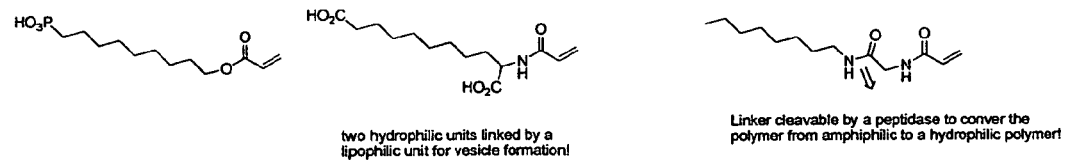

In light of the foregoing, it is an object of the present invention to provide amphiphilic monomers, polymers thereof and/or related methods for their use, micellar assembly and configurations, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is another object of the present invention to provide polymers of the type described herein comprising amphiphilic monomers, such monomers providing spatially-configured hydrophobic and hydrophilic moieties.

It is an object of the present invention to provide a polymeric compound having invertible micellar capability at low critical micelle concentrations, as compared to small molecule surfactants of the prior art.

Other objects, features, benefits and advantages of the present invention will be apparent from this summary and its descriptions of various embodiments, and will be readily apparent to those skilled in the art having knowledge of nanostructured micelle assembly techniques. Such objects, features, benefits and advantages will be apparent from the above as taken into conjunction with the accompanying examples, data, FIGS. and all reasonable inferences to be drawn therefrom.

In part, the present invention can comprise a monomeric compound of a formula

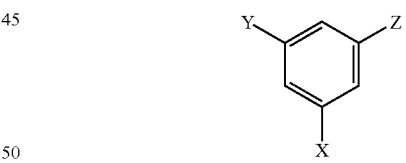

wherein Y is a hydrophilic component, Z is a hydrophobic component, and X is a polymerizable component. Such components would be well known to those skilled in the art made aware of this invention. For instance, component Y can comprise a carboxylic acid/carboxylate moiety (e.g., acetic acid/acetate). In certain embodiments, such as those described herein, component Y can be an oxyacetic acid substituent. Likewise, component Z can comprise an alkylphenyl moiety (e.g., benzyl). In certain embodiments, such as those described herein, component Z can be a benzoxy substituent. Further, component X can comprise an unsaturated moiety, limited only by an ability to undergo polymerization without adversely affecting the chemical or structural integrity of components Y and Z. Accordingly, component X can comprise an alkenyl moiety (e.g., ethenyl, propenyl, etc.).

Alternatively, this invention can comprise a monomeric compound of a formula

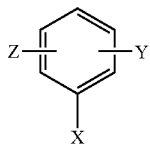

wherein X can be selected from alkenyl and substituted alkenyl moieties; and Y and Z independently comprise and can be independently selected from oxyacetic acid, substituted oxyacetic acid, oxyacetic acid salt, substituted oxyacetic acid salt, oxyacetic acid ester, oxyacetamide, substituted oxyacetamide, poly(ethylene oxide), substituted poly(ethylene oxide), benzoxy, substituted benzoxy, alkoxy and substituted alkoxy moieties, said Y and Z moieties can provide amphiphilic character to the monomer, regardless of position (e.g., meta) with respect to X.

Likewise, other embodiments can comprise a monomeric compound of a formula

wherein X can be selected from acryloyl and substituted acryloyl moieties; and Y and Z independently comprise and can be independently selected from H, alkyl, substituted alkyl, ethanoic acid, substituted ethanoic acid, an ethanoic acid salt, a substituted ethanoic acid salt, ethanoic acid ester, a substituted ethanoic acid ester, ethanoic acid amide, and N-substituted ethanoic acid amide moieties, with Y and Z providing amphiphilic character to the monomer.

Accordingly, the present invention can also comprise an amphiphilic polymeric compound of a formula

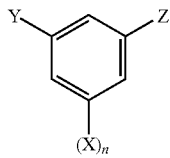

wherein components X, Y and Z are as described above and illustrated elsewhere, herein, and n denotes a numeric plurality of component X. As illustrated herein, such a compound can be homopolymeric, but can also incorporate various other monomers or components, such incorporation limited only so as to not unduly compromise polymoric configuration and/or micellar assembly and inversion of the type described herein. Likewise, such polymers are not limited to monomers having a meta relationship; that is, Y or Z can be ortho or para with respect to X.

The present invention can also provide a system comprising an amphiphilic polymeric compound of the type described herein, and a fluid medium contacting such a polymeric compound. The medium can be polar whether or not ionic, or non-polar. The system can further comprise one or more components in, introduced to and/or at least partially soluble within the fluid medium. Polymer/medium contact can be used to induce interaction with such a component or solute, sequester it within or release it from the polymeric component.

As such, the present invention also provides a method of using an amphiphilic monomeric structure to induce and/or invert polymeric configuration. Such a method comprises providing a polymer comprising monomer moieties and/or substituents of the sort described above; contacting the polymer with one of either a polar or a non-polar fluid medium to induce a first assembled configuration; and optionally contacting the polymer with the other fluid medium to induce a second polymer configuration, inverted with respect to the first. Without limitation to any one theory or mode of operation, and in contrast to rigid amphiphilic polymers of the prior art, it is believed use of monomeric compounds of the sort described herein provide polymeric structures with conformational flexibility sufficient for micellar formation and/or inversion. Various other monomeric compounds, substituents and/or configurations can be used consistent with the preceding, such compounds of the sort but not limited to those provided in FIGS. 1 and 2. As shown in FIG. 2, such compounds can, alternatively, provide two hydrophilic moieties and one hydrophobic moiety, regardless of structural configuration in relation to the polymerizable ethylenic component. (Reference is made to Example 8, below.) An additional benefit available for use of such monomeric compounds is biodegradability of the referenced components and resulting polymers. Accordingly, amphiphilic design and corresponding biocompatibility provides a useful combination for delivery of therapeutic and/or genetic agents. In particular, several compounds of FIG. 2, comprising two hydrophilic moieties, are suitable for corresponding vesicular delivery of polar molecular agents. Such compounds, including those provided in FIG. 2, can also be used in conjunction with the polymeric compounds and systems described above and as further contemplated within the broader scope of this invention.

Consistent with broader aspects of this invention, various systems and methods of this invention can be used in conjunction with polymers comprising monomeric compounds of a formula

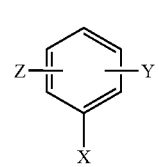

(I)

wherein Y and Z can be independently selected from OH, O, $NHR_1$, $NR_1R_2$, SH, S, C(=O)OH, C(=O)O, C(=O), $SO_3H$, $SO_2$, $E_1L_1$, $E_2L_2$, $P(L_2)_2$, $E_3R_3$, or $E_4R_4$;

$E_1$ is $CH_2$ or $CF_2$;

$E_2$ is $NR_6$, O, S, $N(R_6)C(=O)$, OC(=O) or SC(=O);

$E_3$ is $CHR_7$, $CF_2$, or $CFR_7$;

$E_4$ is $NR_6$, O, S, $N(R_6)C(=O)$, OC(=O) or SC(=O);

$L_1$ is H, $C_1$- about $C_{20}$ alkyl, phenyl, $C_1$- about $C_{20}$ alkyl-substituted phenyl, benzyl, diphenylphosphine-substituted $C_1$- about $C_{20}$ alkyl, $C_1$- about $C_{20}$ perfluoroalkyl, or $C_1$- about $C_{20}$ perfluoroalkyl-substituted phenyl;

L2 is $C_1$- about $C_{20}$ alkyl, phenyl, $C_1$- about $C_{20}$ alkyl-substituted phenyl, benzyl, diphenylphosphine substituted $C_1$- about $C_{20}$ alkyl, $C_1$- about $C_{20}$ perfluoroalkyl, or $C_1$- about $C_{20}$ perfluoroalkyl-substituted phenyl;

$R_1$ and $R_2$ are each independently H or $C_1$- about $C_{20}$ alkyl; $R_3$ is OH, $NH_2$, C(=O)OH, —$SO_3H$, or $PO_3R_7H$; $R_4$ is H, $(CH_2CH_2O)x-R_8$, $(CH_2CH_2O)x-CH_2CH_2—NR_9R_{10}$; $(CH_2CH_2O)x-C(=O)NR_9R_{10}$, an amino acid, a polypeptide, a nucleic acid, a polynucleic acid, biotin, sugar, a polysaccharide, a carboxylic acid-substituted $C_1$- about $C_{10}$ alkyl, an amino-substituted $C_1$- about $C_{10}$ alkyl, a hydroxy-substituted $C_1$- about $C_{10}$ alkyl, a sulfonic acid-substituted $C_1$- about $C_{10}$ alkyl, a phosphinic acid-substituted $C_1$- about $C_{10}$ alkyl, a phosphonic acid-substituted $C_1$- about $C_{10}$ alkyl, a nitrogen-heterocycle, a nitrogen-heterocycle-substituted $C_1$- about $C_{10}$ alkyl, or a trialkylammonium-substituted $C_1$- about $C_{10}$ alkyl; $R_5$ is $C_1$- about $C_{20}$ alkyl, phenyl, methylphenyl, or $CF_3$; $R_6$ is H, $C_1$- about $C_{20}$ alkyl, or $C_1$- about $C_{20}$ perfluoroalkyl; $R_7$ is H or C1-C3 alkyl; $R_8$, $R_9$, and $R_{10}$ are each independently H or $C_1$- about $C_3$ alkyl; x is an integer having a value in the range of 0 to about 20; with the proviso that: when Y is OH, O, $NHR_1$, $NR_1$, SH, S, C(=O)OH, C(=O)O, C(=O), $SO_3H$, or $SO_2$, $X_2$ is OH, O, $NHR_1$, $NR_1$, SH, S, C(=O)OH, C(=O)O, C(=O)$Z_2$, C(=O), $SO_3H$, $SO_2Z_2$, or $SO_2$, $Y_1$ and $Y_2$ are $E_1L_1$, $E_2L_2$, $P(L_2)_2$, $E_3R_3$ or $E_4R_4$; when Z is OH, O, $NHR_1$, $NR_1$, SH, S, C(=O)OH, C(=O)O, C(=O), $SO_3H$, or $SO_2$, $Y_2$ is OH, O, $NHR_1$, $NR_1$, SH, S, C(=O)OH, C(=O)O, C(=O)$Z_2$, C(=O), $SO_3H$, $SO_2Z_2$, or $SO_2$, $X_1$ and $X_2$ are $E_1L_1$, $E_2L_2$, $P(L_2)_2$, $E_3R_3$ or $E_4R_4$; and X is a polymerizable moiety, optionally coupled to the phenyl component with Y or Z such that a resulting polymer can comprise e.g., a styrenyl, acrylate, methacrylate, or acrylamide moiety.

Whereas several monomeric embodiments are shown in a meta-substitution pattern, when X is in the 1 position of the phenyl ring, Y can be in the 2 or 3 position of the phenyl ring, and Z can independently be in the 4, 5 or 6 position of the phenyl ring. Regardless, phenyl can be coupled to the polymer backbone or Y or Z to the phenyl, with a linker moiety cleavable under certain conditions. Non-limiting examples include disulfide linkage, ester linkage, peptide linkage, acetal moiety, or ketal moiety.

Additional embodiments can comprise monomers of a formula

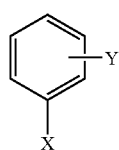

(II)

wherein X and Y can be as provided, above, and of X is of the 1 position of the phenyl ring, Y can be at the 2, 3 or 4 position of the phenyl ring Additional embodiment can, yet, further comprise monomers of a formula

(III)

wherein X, Y and Z can be as provided, above.

Further, and without limitation, additional embodiments can comprise monomers of a formula

(IV)

where A can be selected from O, NH, and S, and X and Y can be as provided, above.

Without limitation, illustrative embodiments of (I)-(IV) can be considered in conjunction with the following monomeric compounds:

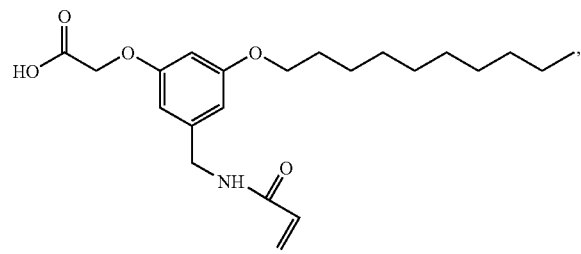

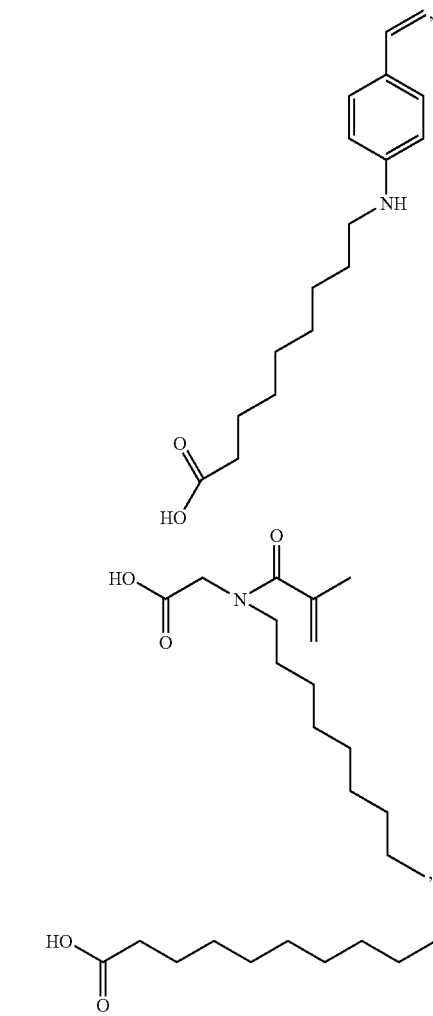

, and

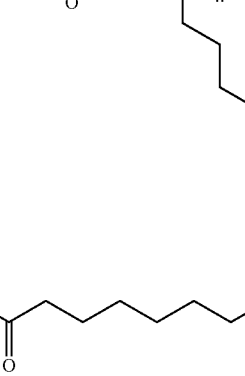

Accordingly, monomeric compounds and corresponding polymers of this invention are limited only by their amphiphilic properties, function and behavior, as illustrated herein, in a fluid or solvent medium or, alternatively, as provided isolated from any particular fluid medium, or alone or in conjunction with a film or composition, as can be provided in conjunction with a substrate. Such monomers and corresponding polymers, regardless of moiety or substituent identity, can be prepared as described herein or through use of straightforward modifications of such synthetic techniques, as would be understood by those skilled in the art made aware of this invention. Other representative, non-limiting compounds in accordance herewith are provided in FIGS. 2A-B.

With respect to either the monomer compounds, polymers, systems and/or methods of the present invention, the moieties or substituents thereof can suitably comprise, consist of or, or consist essentially of any of the aforementioned moieties, substituents and functional groups thereof. Each such monomer or polymer compound or moiety/substituent thereof, is compositionally distinguishable, characteristically contrasted and can be practiced in conjunction with the present invention separate and apart from one another. Accordingly, it should also be understood that inventive monomers, polymers, systems and/or inventions, as illustratively disclosed herein, can be practiced or utilized in the absence of any one compound, moiety and/or substituent which may or may not be disclosed, referenced or inferred herein, the absence of which may not be specifically disclosed.

DETAILED DESCRIPTION OF CERTAIN EMBODIMENTS

In comparison to poly(styrene-co-acrylic acid) block copolymers of the prior art, various aspects of this invention were initially demonstrated incorporating carboxylic acid and benzyl moieties, the hydrophilic and hydrophobic functionalities in polyacrylic acid and polystyrene respectively, within the same monomer of a homopolymer—to provide an interesting intramolecular phase separation perspective. Accordingly, a styrene-based monomer shown by the structure 1a (FIG. 1) was prepared. The hydrophilic carboxylic acid functionality, the hydrophobic benzyl moiety, and the polymerizable olefinic bond are all placed at meta-positions with respect to each other on a benzene ring. Such a design strategy is that the relative placement of these three functionalities should facilitate the phase segregation of the amphiphilic moieties within the polymer assembly. Monomers 1a and 1b, which have the carboxylic acid functionality in its masked form for synthetic reasons, was derived from 3,5-dihydroxybenzoic acid in six steps. Free radical polymerization of the monomer 1a using AIBN (1 mol. %) as the initiator afforded polymer 2a, with $M_n$=57,000, PDI=2.3, and an average DP=167, as determined by size exclusion chromatography (SEC) against polystyrene standards. Hydrolysis of polymer 2 afforded the carboxylic acid based polymer 3. Addition of 1-2 equivalents of bases such as NaOH or KOH per carboxylic acid functionality renders the polymer soluble in water.

Interestingly, polymer 3 was found not to be soluble in apolar solvents such as dichloromethane and toluene. However, addition of one equivalent of base along with 2-3 equivalents of water rendered the resultant carboxylate polymer soluble in these apolar solvents. The observed solubility characteristics are believed to be the result of formation of a micelle-like structure in water, in which the hydrophilic carboxylate groups are exposed to the bulk solvent and the hydrophobic benzyl substituents are tucked in the interior of an assembly (Scheme 1). Similarly, an inverted micelle-like structure is found in apolar solvents, in which the functional group placements are reversed.

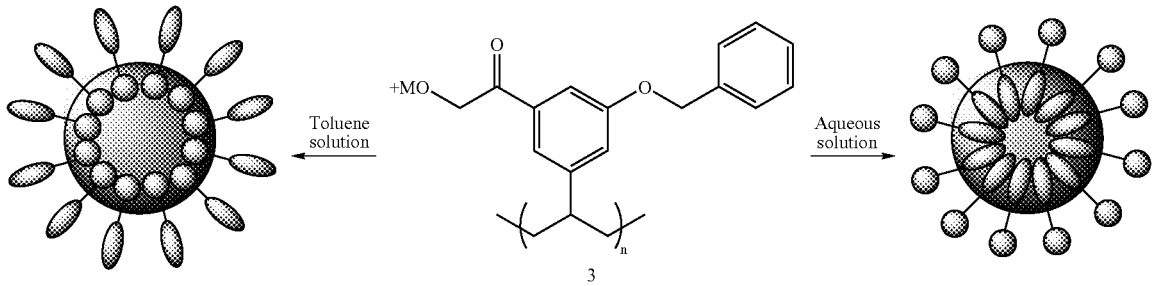

Scheme 1. Schematic representation of micelle-type and inverse-micelle type assemblies As an extension of the foregoing, polymer compounds of this invention can be used to encapsulate a range of agents or component molecules and for delivery and/or release with a stimulus. More specifically, as demonstrated in several of the following examples, this invention can involve encapsulating hydrophobic molecules in a polar solvent environment or, alternatively, hydrophilic molecules in a polar surrounding, either of which can be released upon a change in solvent polarity, e.g., a change in pH. The polymers of this invention can provide opportunities in targeted drug delivery. For example, such an approach can be used for the targeted delivery of chemotherapeutic agents to tumor cells.

For instance, contrary to the existing theory that high molecular weight macromolecules cannot enter tumors, polymers of molecular weights up to 800 KDa have been shown to have access to tumors. Tumor vessels are leaky and therefore allow macromolecular uptake that is not possible in healthy tissues. Also, the lack of effective tumor lymphatic drainage prevents the clearance of the macromolecules and therefore promotes the accumulation of the macromolecule-drug conjugate. This so-called "enhanced permeation retention (EPR)" effect has been demonstrated by illustrating that tumor cells selectively uptake and retain the macromolecule-drug conjugates at a much higher percentage than the free drug. Polymers of the prior art, including dendrimers, have been used as macromolecular scaffolds for this purpose, where functional groups in the dendrimer are attached to the drug molecule with a peptidyl connectivity cleavable by proteases. The EPR method of targeted drug delivery utilizes the time a polymer-drug conjugate spends in a biological system, before entering a tumor cell. During this waiting period, it is desirable that the drug is not degradatively released from the polymer, instead it effectively hides inside a hydrophobic pocket until the dendrimer-drug conjugate reaches the tumor. Note that many of the anti-cancer drugs are hydrophobic (e.g., doxorubicin and taxol). Since the pH is lower in a tumor and the lysosome, the dendrimer-drug connectivity will be exposed for cleavage upon entry into the tumors. (The pH in the tumors is about 6.7; pH in a healthy cell is about 7.4; pH in a lysosome is about 5.0.)

One possible mechanism by which polymer-drug connectivity is exposed involves the incorporation of a hydrophobic pH-sensitive moiety. For example, if amino groups are incorporated in these dentritic interiors, the amino group would be protonated. The resultant ammonium cation becomes hydrophilic and charge accumulation in the polymeric interior would cause charge-charge repulsion changing polymer conformation. However, such polymers, especially dendrimers, are synthetically difficult and present associated access and application issues.

As a departure from the art, a polymer of this invention (e.g., where Z comprises an alkylamine moiety pendant to an acrylamide polymer) can be used for delivery and/or release of a therapeutic agent or component incorporated with or encapsulated therein. While such results can be achieved utilizing such polymers and/or moieties upon change in pH, delivery/release can also be achieved using various other polymers upon change in fluid/solvent media. For instance, as mentioned above and illustrated below, lipophilic/hydrophilic compounds can be encapsulated in a polar or aqueous medium. Likewise, polymers of this invention can be configured about a hydrophilic component or agent in a hydrophobic/non-polar medium. Regardless, a change in external environment experienced by the polymer can serve to change or invert configuration and release an associated agent or component. In addition to various therapeutic applications, this invention can find comparable utility for controlled delivery/release in the areas of cosmetics, fragrances, fertilizers and pesticides, among others-all through the monomeric compounds and polymers herein.

Without limitation, embodiments of this invention can also find utility as a phase transfer agent in fluorocarbon solvents. (See Example 7.) More generally, various polymers in this invention can be used as solubilizing agents; that is, to dissolve or uniformly disperse molecules into a media otherwise incompatible. Such a media can be a solvent, a surface, or another polymer system, whether polar or non-polar. For instance, fluorophores are commonly used for imaging and biological and material applications. However, such compounds are hydrophobic and not sufficiently soluble in water. Therefore, a useful strategy can be to configure polymers of this invention about the fluorophores, to solubilize that in water or other polar solvents. Inversely, a comparable strategy could also be used to dissolve hydrophilic fluorophores in non-polar solvents. It would be understood by those skilled in the art and made aware of this invention, other possible applications include, without limitation, tissue engineering, extraction of waste components or analytes from water systems (i.e., for purification or sensing applications), nanosynthesis and nanoparticle protection, fluorescent imaging, emulsification techniques, etc.

Without limitation, various compounds of this invention can be described with reference to Tables 1 and 2, below. In Table 1, X is alkenyl (or substituted alkenyl), and Y moieties are shown as the acid salts, without limitation as to the counter cation, but it will be understood by those skilled in the art that such moieties can also include the acid, ester, substituted ester, amide, substituted amide and homologs of any such moiety. Likewise, the Z moiety of any such compound can further include homologs or structural isomers thereof. Consistent with one or more aspects of this invention, in any such compound can comprise any Y moiety in combination with any Z moiety, providing such a compound comprises one hydrophilic moiety and one hydrophobic moiety. While the compounds of Table 1 are described with possible monomeric structures, any such monomer can be used, as described herein with other like or different monomers to provide a corresponding amphiphilic polymer compound. Such considerations also apply to the compounds of Table 2, wherein X is an acryloyl (or substituted acryloyl) moiety. Polymers of one or more of one or more such acryloyl monomers, or with any of the alkenyl monomers, can be prepared as described herein to impart a degree of biodegradability to such compounds.

TABLE 1

| X | Y | Z |
|---|---|---|
| $CH_2 = CH$ (alkenyl) | $OCH_2COO^-$ (oxyacetate) $OCHRCOO^-$ (substituted oxyacetate), where R is linear alkyl or branched alkyl $O(CH_2CH_2O)_n CH_2COO^-$ (oxyacetate substituted poly(ethylene oxide)), where $n \geq 1$ $O(CH_2CH_2O)_n R$, where R is H, alkyl, hydroxyl or amine terminal group, and $n \geq 1$ | $OCH_3$ (alkoxy) $O(CH_2)_n(CHR)_{n'}CH_3$ (substituted alkoxy) where R is linear or branched alkyl and n and n' independently range from 0 to about 20 $O\ CH_2Ar$ (benzoxy), where Ar is aryl or substituted aryl $OCHR\ Ar$ (substituted benzoxy), where R is linear or branched alkyl and Ar is aryl or substituted aryl |

TABLE 2

| X | Y | Z |
|---|---|---|
| $CH_2 = CHC(O)$ (acryloyl) | $CH_2COO^-$ (ethanoate) $CHRCOO^-$ (substituted ethanoate), where R is linear or branched alkylamine, alkylamidoalkyl, benzyl, substituted benzyl | H $(CH_2)_nCH_3$ where n ranges from about 2 ($C_3$) to 19 ($C_{20}$) $(CH_2)_n(CHR)_{n'}CH_3$ (substituted alkyl) where R is linear or branched alkyl and n and n' independently range from 0 to about 20 $CH_2Ar$ (benzyl), where Ar is aryl or substituted aryl $(CH_2)_n COO^-$ (alkyl carboxy) where n ranges from about 2 to about 20 |

EXAMPLES OF THE INVENTION

The following non-limiting examples and data illustrate various aspects and features relating to the amphiphilic monomeric compounds, polymers, polymeric systems and/or related methods of the present invention, including the assembly of invertible nanostructured micelles, as are available through the methodologies and techniques described herein. In comparison with the prior art, the present compounds, systems and/or methods provide results and data which are surprising, unexpected and contrary thereto. While the utility of this invention is illustrated through the use of several monomers and corresponding polymers, it will be understood by those skilled in the art that comparable results are obtainable with various other hydrophobic and hydrophilic monomeric substituents, and the corresponding monomers and polymers, as are commensurate with the scope of this invention.

General Methods

All reagents were commercially available and used as received unless stated otherwise. $^1$H-NMR spectra were recorded on a 400 MHz NMR spectrometer using residual proton resonance of the solvents as internal standard. Chemical shifts are reported in parts per million (ppm). $^{13}$C-NMR spectra were proton decoupled and recorded on a 100 MHz NMR spectrometer using the carbon signal of the deuterated solvent as the internal standard. Mass spectra were obtained at the Molecular Weight Characterization Facility at University of Massachusetts. The molecular weights of the polymers were determined by size exclusion chromatography on a single injector mode GPC, using THF as eluent and toluene as the internal reference; polystyrene standards were used for calibration and output was received and analyzed using a RI detector. The monomers 1a and 1b were synthesized starting from 3,5-dihydroxybenzoic acid in six steps.

Example 1

With reference to FIG. 1, the synthesis of monomer 1a and 1b:

Example 1a

Synthesis of Compound 5

The amphiphilic monomer was synthesized from commercially available 3,5-dihydroxybenzoic acid (4) using ethanol and catalytic amount of fuming sulfuric acid.

Example 1b

Synthesis of Compound 6

Ethyl-3,5-dihydroxybenzoate 5 (27.3 g, 150 mmol) was dissolved in acetone (750 mL). To this solution were added K$_2$CO$_3$ (20.7 g, 150 mmol) and 18-Crown-6 (1.9 g, 7.5 mmol) and stirred for 5 min. To this mixture, benzyl bromide (14.2 mL, 120 mmol) was added and stirred to reflux for 8 h. The reaction mixture was then cooled to room temperature and the solvent was evaporated to dryness. To this residue, water and diethylether were added and stirred for 30 min. The organic layer was separated and aqueous layer was extracted with diethylether. The combined organic layer was washed with water and brine solution. The organic layer was then evaporated to dryness and purified by silica gel chromatography to Synthesis of monomer 1a and 1b:

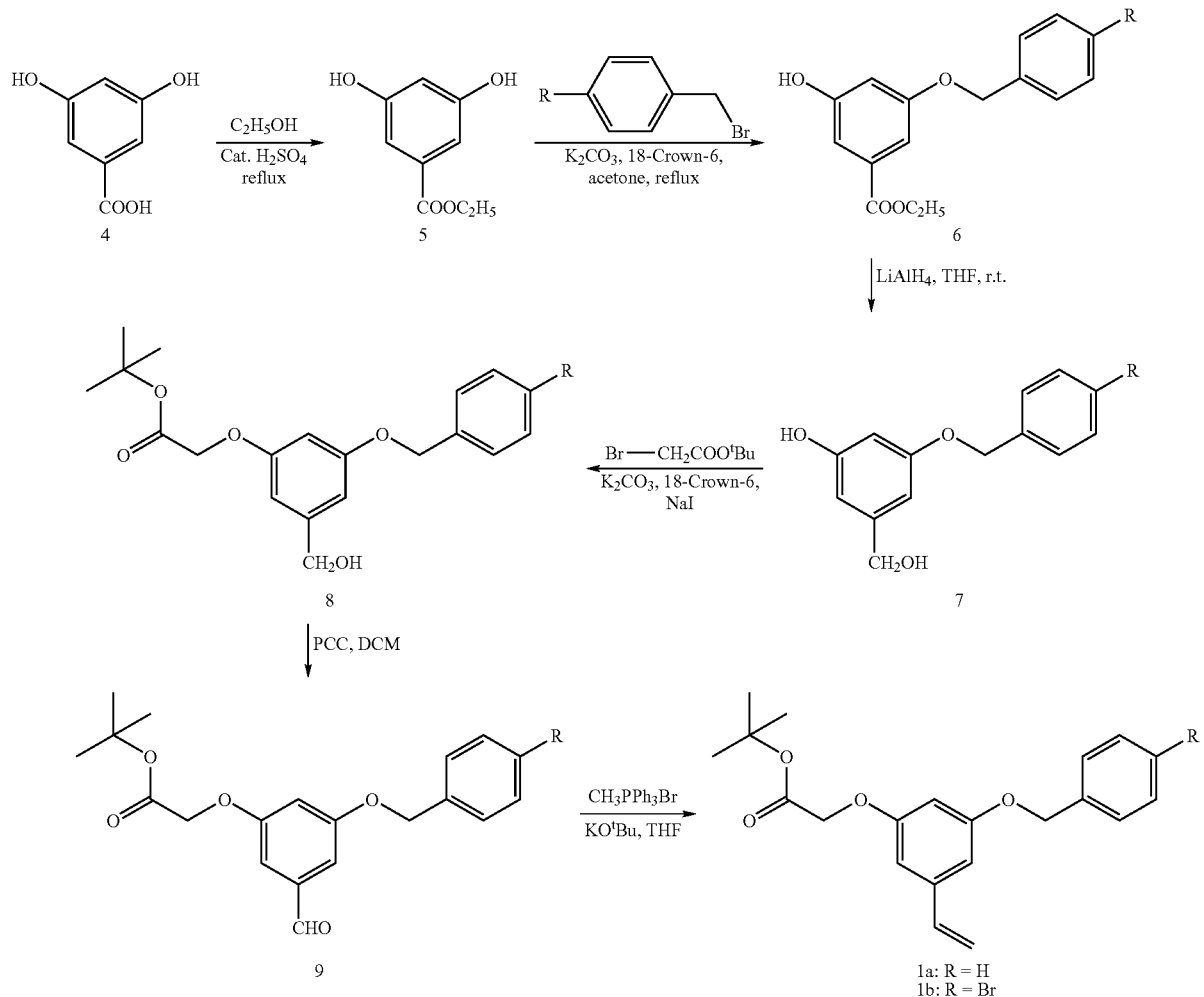

afford 14.5 g of 6 (35%). The major by-product of this reaction is the compound, where two benzyl groups are added to the two phenolic groups of compound 5. $^1$H NMR (400 MHz, CDCl$_3$) δ 7.43-7.31 (m, 5H), 7.26-7.25 (m, 1H), 7.16-7.15 (m, 1H), 6.67 (t, J=2.4 Hz, 1H), 5.01 (s, 2H), 4.35 (q, J=7.2 Hz, 2H), 1.37 (t, J=7.2 Hz, 3H); $^{13}$C NMR (100 MHz, CDCl$_3$) δ 166.8, 159.9, 157.0, 136.4, 132.2, 128.6, 128.1, 127.5, 109.5, 108.1, 107.3, 70.2, 61.4, 14.1.

Example 1c

Synthesis of Compound 7

LiAlH$_4$ (3.0 g, 79 mmol) was taken in dry THF (200 mL) and cooled to 0° C. Compound 6 (14.3 g, 53 mmol) dissolved in dry THF (200 mL) was added drop wise to the above solution for 30 min. It was allowed to stir at room temperature for 12 h. The reaction mixture was quenched with ethyl acetate followed by water. The precipitated material was filtered and washed with ethyl acetate. The filtrate was then taken in a separating funnel. The organic layer was separated and the aqueous layer was extracted with ethyl acetate. The combined organic layer was washed with water, followed by brine solution. The organic layer was evaporated and purified by silica gel column chromatography to afford 10.8 g of compound 7 (89%). $^1$H NMR (400 MHz, CDCl$_3$) δ 8.28 (s, 1H), 7.47-7.29 (m, 5H), 6.53 (s, 1H), 6.47 (s, 1H), 6.36 (s, 1H), 5.0 (s, 2H), 4.52 (s, 2H); $^{13}$C NMR (100 MHz, CD$_3$COCD$_3$) δ 160.8, 159.1, 145.8, 138.4, 129.0, 128.3, 128.1, 106.8, 104.7, 101.2, 70.1, 64.5.

Example 1d

Synthesis of Compound 8

Compound 7 (4.8 g, 21 mmol) was dissolved in acetonitrile (60 mL). To this solution were added, K$_2$CO$_3$ (3.5 g, 25.2 mmol), NaI (3.2 g, 21 mmol) and 18-Crown-6 (0.33 g, 1.25 mmol) followed by tert-butyl bromoacetate (3.1 mL, 21 mmol). The reaction mixture was refluxed for 36 h. It was then cooled to room temperature and solvent was evaporated to dryness. The residue was partitioned between water and CH$_2$Cl$_2$. The organic layer was separated, and the aqueous layer was extracted with CH$_2$Cl$_2$. The combined organic layer was dried over Na$_2$SO$_4$ and evaporated to dryness. The crude product was purified by silica gel chromatography to afford 7.0 g of compound 8 (97%). $^1$H NMR (400 MHz, CDCl$_3$) δ 7.41-7.38 (m, 5H), 6.64 (bs, 1H), 6.52 (bs, 1H), 6.49 (t, J=2.4 Hz, 1H), 5.04 (s, 2H), 4.63 (s, 2H), 4.50 (s, 2H), 1.49 (s, 9H) $^{13}$C NMR (100 MHz, CDCl$_3$) δ 167.9, 160.0, 159.1, 143.4, 136.7, 128.5, 127.9, 127.4, 106.3, 105.1, 82.3, 70.0, 65.6, 65.1, 28.0.

Example 1e

Synthesis of Compound 9

To a stirred solution of compound 8 (7.0 g, 20.5 mmol) in dichloromethane (100 mL) was added pyridinium chlorochromate (5.2 g, 25 mmol). It was stirred at room temperature for 3 h. The reaction mixture was filtered over alumina and the filtrate was evaporated and purified by silica gel chromatography to afford 6.2 g of compound 9 (88%). $^1$H NMR (400 MHz, CDCl$_3$) δ 9.88 (s, 1H), 7.4-7.34 (m, 5H), 7.13-7.12 (m, 1H), 6.98-6.97 (m, 1H), 6.82 (t, J=2.4 Hz, 1H), 5.09 (s, 2H), 4.5 (s, 2H), 1.49 (s, 9H) $^{13}$C NMR (100 MHz, CDCl$_3$) δ 191.5, 167.4, 160.3, 159.5, 138.3, 136.1, 128.6, 128.2, 127.5, 109.3, 108.5, 107.1, 82.7, 70.3, 65.6, 27.9.

Example 1f

Synthesis of Compound 1a

Commercially available CH$_3$PPh$_3$Br (8.2 g, 22.8 mmol) was taken in dry THF (75 mL) and KO$^t$Bu (2.5 g, 22.8 mmol) was added to this under nitrogen atmosphere. This reaction mixture was stirred for 20 min and a solution of compound 9 (6.0 g, 17.6 mmol in 75 mL of dry THF) was added slowly with syringe to the above solution. The reaction mixture was further stirred at room temperature for 4 h. The reaction mixture was filtered and the filtrate evaporated and purified by silica gel chromatography to afford 5.2 g of compound 1a (87%). $^1$H NMR (400 MHz, CDCl$_3$) δ 7.43-7.30 (m, 5H), 6.63-6.53 (m, 3H), 6.46 (t, J=2.46 Hz, 1H), 5.68 (d, J=8.66 Hz, 1H), 5.23 (d, J=6.0 Hz, 1H), 5.02 (s, 2H), 4.48 (s, 2H), 1.47 (s, 9H) $^{13}$C NMR (100 MHz, CDCl$_3$) δ 167.8, 159.9, 159.0, 139.6, 136.7, 136.5, 128.8, 127.9, 127.4, 114.4, 106.3, 104.8, 101.4, 82.3, 70.0, 65.6, 27.9.

Example 1g

The monomer 1b was synthesized following the above procedures.

Polymerization of the Monomers 1a and 1b

To a 1 g/mL solution of monomer 1a (1.6 g, 4.72 mmol) in toluene was added AIBN (0.0076 g, 0.047 mmol) and the reactor was degassed by 4 freeze-thaw cycles before transferring to an oil-bath pre-heated to 110° C. The reaction mixture was stirred for 24 h at this temperature and then allowed to cool down to room temperature. Solvent was removed under reduced pressure before it was cooled, to get the product polymer 2a (n>1). The product was characterized for structure and molecular weight without further purification. SEC (polystyrene/THF): ‾M$_n$ 57,000, ‾M$_W$ 131,500, PDI 2.3; $^1$H-NMR (400 MHz, CDCl$_3$) δ 7.24-7.16 (m, 5H), 6.0-5.7 (m, 3H), 4.59 (s, 2H), 4.12 (s, 2H), 1.47-1.41 (m, 3H), 1.33 (s, 9H).

To a 1 g/mL solution of monomer 1b (1.6 g, 4.72 mmol) in toluene was added AIBN (0.0076 g, 0.047 mmol) and the reactor was degassed by 4 freeze-thaw cycles before transferring to an oil-bath pre-heated to 110° C. The reaction mixture was stirred for 24 h at this temperature and then allowed to cool down to room temperature. Solvent was removed under reduced pressure before it was cooled, to get the product polymer 2b (n>1). The product was characterized for structure and molecular weight without further purification. SEC (polystyrene/THF): ‾M$_n$ 47,800, ‾M$_W$ 119,500, PDI 2.5; $^1$H-NMR (400 MHz, CDCl$_3$) δ 7.33-7.06 (m, 4H), 6.02-5.63 (m, 3H), 4.54 (s, 2H), 4.18 (s, 2H), 1.56-1.45 (m, 3H), 1.38 (s, 9H).

Example 1h

Hydrolysis of the Polymers (2a and 2b)

To a solution of polymer 2a (0.3 g, 0.88 mmol) in Tetrahydrofuran (15 mL) was added aqueous potassium hydroxide (0.5 g, 8.8 mmol) dissolved in water (3 mL). Methanol (6 mL) was then added to this two-phase system to give a homogeneous solution. This mixture was then heated at reflux for 12 h. The reaction mixture was evaporated to dryness and the residue redissolved in water (15 mL) and the mixture heated at reflux for another 24 h. After cooling to room temperature, the reaction mixture was acidified with 2N HCl. The precipitate formed was collected by vacuum filtration and dried to afford polymer 3a (n>1). Yield: 0.26 g (95%). $^1$H-NMR (400

MHz, THF-d$_8$) δ 7.29-7.19 (m, 5H), 6.20-6.00 (m, 3H), 4.75 (s, 2H), 4.38 (s, 2H), 1.49-1.32 (m, 3H).

Following the above procedure the polymer 2b (0.35 g, 0.84 mmol) was hydrolyzed to afford the polymer 3b (n>1). Yield: 0.31 g (94%). $^1$H-NMR (400 MHz, THF-d$_8$) δ 7.39-7.20 (m, 4H), 6.17-5.98 (m, 3H), 4.69 (s, 2H), 4.39 (s, 2H), 1.49-1.32 (m, 3H).

Example 1i

Sample Preparation for TEM Experiments

TEM measurements were performed using a JEOL 100CX 100 KV TEM. To prepare solutions for doing TEM for the normal micelle-like structures the polymers were dissolved in appropriate amount of water with KOH/CsOH as the base. For each COOH unit present in the polymer 1.5 equivalents of KOH/CsOH were added in order to form the carboxylate salts, which is soluble in water. This solution was then sonicated for 1-1.5 h to ensure solubility of the polymers. To prepare the solutions for doing TEM of inverted micelle-like particles, an appropriate amount of polymer was taken with calculated amount of toluene. To make the polymer soluble in non-polar solvent (toluene here) 1.5-2 equivalents of KOH/CsOH was added to the polymer solution, along with 3 equivalents of water, for each carboxylic acid group present in the measured amount of polymer. This solution was then sonicated for 4 hours to ensure a homogeneous solution. Control experiments without the polymers were also carried out in all cases. Samples were prepared by depositing aqueous or toluene solutions of the amphiphilic polymers onto copper EM grid that had been pre-coated with a thin film of Formvar and then coated with carbon. Water/Toluene was evaporated from the grids by leaving it under atmospheric pressure for one day.

Example 2

Figure 3:
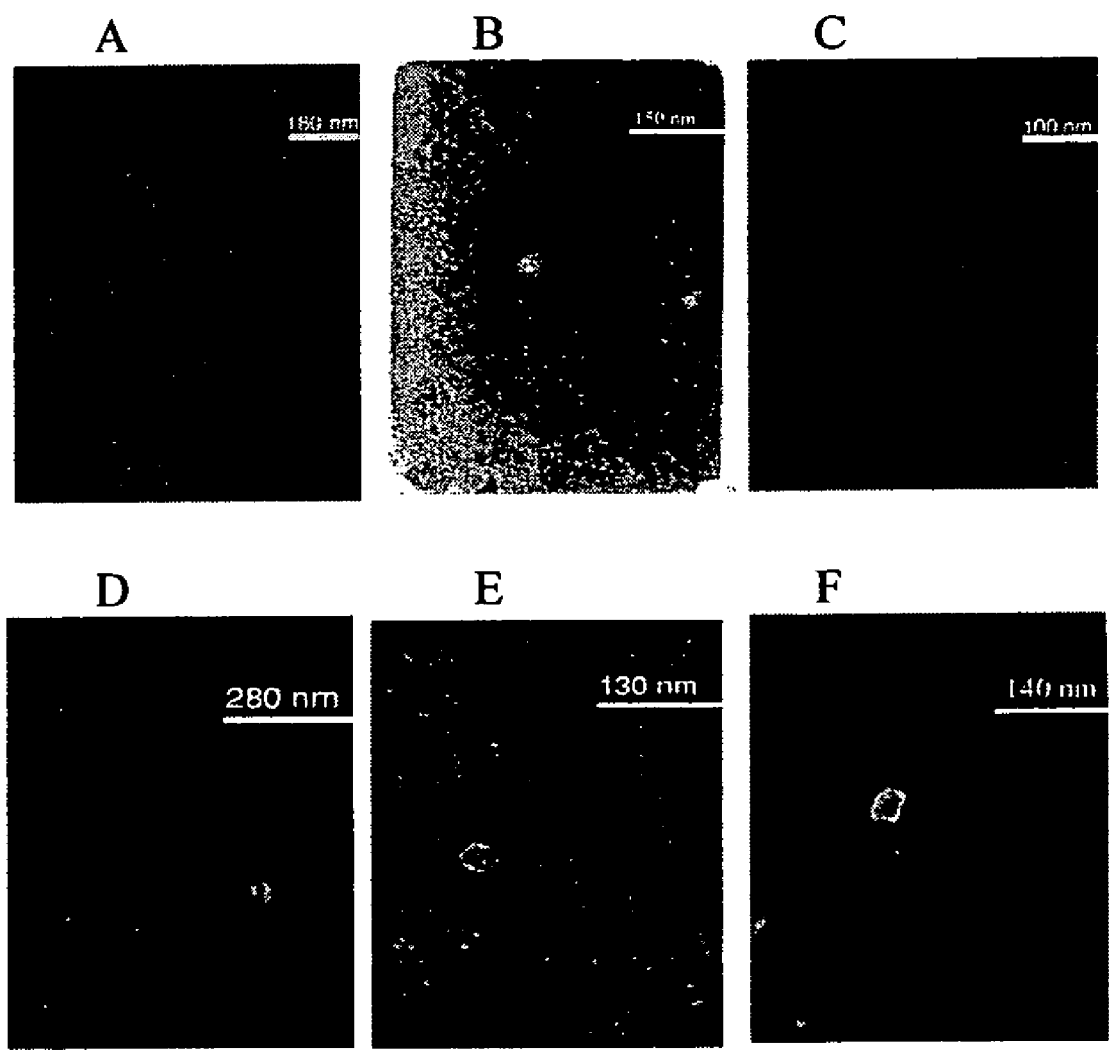
FIGS. 3A-F. TEM images of the micelle-like and inverted micelle-like structures formed by polymers 3a and 3b, FIG. 1. (A) Image of normal micelle-like particle from aqueous solution of the polymer 3a (M=K). (B) Image from an aqueous polymer 3a (M=Cs). (C) Image of an inverted micelle-like particle formed by a toluene solution of the polymer 3a (M=K). (D) Image from a toluene solution of polymer 3a (M=Cs). (E) Image from an aqueous solution of the polymer 3b (M=K). (F) Image from a toluene solution of the polymer 3b (M=K).
Figure 6:
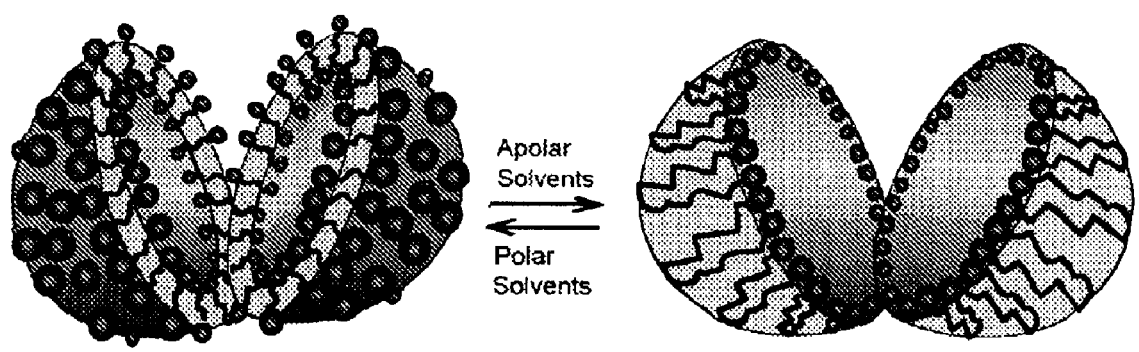
FIG. 6. A schematic representation with the spheres depicting connected hydrophilic moieties, with reference to Example 15.

To investigate the structure of the assemblies the darker contrast provided by heavy atoms in TEM images was used as the probe. In order to identify the placement of the hydrophilic carboxylic acid moiety, polymer 3a (M=H) was treated with CsOH to convert the acid to the corresponding carboxylate salt. The resulting Cs$^+$ counterion is a high atomic weight species that should provide the necessary contrast to identify the placement of the hydrophilic functionality within polymer 3. In this case, the aqueous solution of the polymer (micelle-like assembly) would place the heavier Cs$^+$ counter ion at the corona to afford a dark ring. The experimental observations correspond to this structure as shown by comparing FIGS. 3A and 3B, which are obtained from aqueous solutions containing KOH and CsOH respectively. Note the presence of dark ring around the particles in corona in FIG. 3B relative to the core; no such contrast could be seen in FIG. 3A. Similarly, the inverse micelle-type structure should place the carboxylate moiety and thus the Cs$^+$ counter ions at the core. This placement should afford a dark spotted core in the TEM image. As expected, the CsOH based toluene solution (FIG. 3D) exhibits the image containing a darker core spot compared to that derived from KOH (FIG. 3C).

Example 3

The structural hypothesis also suggests that the hydrophilic carboxylic acid unit and the hydrophobic benzyl moiety will be placed on the opposite sides of the polymer backbone in solvents of different polarity. While the above experiments show the position of the hydrophilic carboxylic acid moieties, it does not provide information on whether the benzyl moieties are placed on the opposite face. For this purpose, we synthesized polymer 3b (M$_n$=41,410; PDI=2.5; average DP=114), which is similar to the polymer 3a (FIG. 1) but with an additional bromine functionality in the 4-position of the hydrophobic benzyl substituent, was synthesized. Assemblies obtained from both aqueous and toluene solutions of 3a and 3b were then compared using TEM. The locale where the bromine atoms are concentrated should exhibit a higher contrast in TEM images. If the hydrophobic benzyl moieties are directed towards the interior in an aqueous solution, the image for polymer 3b should have a darker spotted core relative to 3a (Scheme 1). This was indeed the observed result, as could be seen by comparing the images in FIGS. 32A and 3E obtained from aqueous solutions of polymers 3a and 3b respectively. Note that the images obtained from polymer 3a exhibit uniform darkness, whereas the images from polymer 3b shows a darker core compared to the corona. Similarly, if the hydrophobic benzyl moieties are directed towards the exterior in the inverse micelles, the heavier bromine functionalities in 3b are now placed at the corona. The resulting image for the polymer 3b should exhibit a dark ring in the corona relative to 3a (Scheme 1). The images in FIGS. 3C and 3F, obtained from toluene solutions of polymers 3a and 3b respectively, are consistent with the expected features.

Example 4

The spatial distribution of the dark corona, which is indicative of the spatial distribution of the heavy atom species, is about 5 nm for an average particle size of 55 nm. (Particle sizes at 10$^{-6}$ M concentration of the polymer ranged from 30 nm to 80 nm. The average particle sizes were determined by measuring an average of about 50 particles in the TEM images.) However, the darker core from FIGS. 3D and 3E seem to be distributed throughout the interior. Note that the hydrophobic and the hydrophilic functionalities are stitched together within the same monomer in polymers 3a and 3b. Therefore, it would be expected that the spatial distribution of the interior groups of the assembly closely follow the distribution of functionalities in the corona. Close examination of the normal micelle-like structure in FIG. 3E using a density profiling software ImageJ indicated that the dark spot within FIG. 3E is not uniformly distributed. (ImageJ is free software that can be downloaded from the National Institute of Health web site (http://www.nih.gov).) In fact there is a darker ring followed by a lighter gray core in these assemblies. Thus, the distribution of the bromophenyl functionality within a micelle-like assembly is consistent with the spatial distribution of the carboxylate groups indicated in Fig. eB. However, similar density profiling of the spots in Fig. eD indicated a uniform distribution of darkness at the core. This is not surprising, since the contrast providing Cs$^+$ ions are not covalently attached to the polymer backbone and the solvated ion is likely to be distributed throughout the water filled core.

Example 5

Dilution studies with these micelle-like and inverted micelle-like structures were also done. The solutions made for both normal and reverse micelle were of the concentration of 10$^{-6}$ M. In order to study the structural integrity of the micelle-like and inverted micelle-like particles, both the solutions were diluted to 10$^{-9}$ M and studied by TEM. The TEM images of these are shown in FIGS. 4A and 3B. Comparing FIG. 4A with FIG. 3E shows the particle size and morphology remains same even diluting the system 1000 times. Similar observation is given for inverted micelle-like particles. The sizes of the particles for both the normal and inverted micelle-like structures were calculated by taking an average of about 50 samples for each type of the particles. It was observed that the overall sizes of the particles also remain the same upon dilution.

Example 6

Demonstrating various aspects relating to the methods and systems of this invention, nanostructured polymers comprising monomeric compounds have been used to sequester hydrophobic dye components in water and, conversely, hydrophilic dye components in a number of organic solvent media, thereby illustrating a use of the present invention in conjunction with the selective interaction and/or delivery of a specific solvent-carried component. Such nanostructured assemblies and their corresponding component interactions can be selected by choice and/or alteration of the fluid or liquid medium used therewith.

Example 7

Another embodiment of this invention can be used in a number of separation techniques or to perform phase transfer catalysis in fluorocarbon solvents. Classical phase transfer catalysis reactions involve reaction between a lipophilic substrate and a hydropohilic reagent. There are commercial interests in performing this reaction in a fluorocarbon solvent or supercritical carbon dioxide. Neither lipophilic nor hydrophilic compounds are very soluble in either of these solvents. Various polymers of this invention can provide a nanoscale environment to carry out this reaction. Where component C of a monomeric compound is fluorinated, one face of the corresponding polymer would contain fluorocarbon chains, where as the other face contains a mixture of lipophilic and hydrophilic functionalities. The conformation of the polymer in a fluorocarbon solvent would provide a nanoscale environment in the micelle-type interior that contains both lipophilic and hydrophilic substituents. Therefore, the polymer can sequester both lipophilic and hydrophilic reactant compounds and confine them together in a nanoscale environment, to enhance bimolecular collisions and catalyze the desired reaction. Similar reactions can be carried out in supercritical carbon dioxide, since it preferentially solubilizes fluorocarbon substituents.

Example 8

With reference to FIG. 2, amphiphilic compounds of this invention and their corresponding polymers can be prepared using synthetic techniques of the sort provided below, variations of which for any particular monomer and/or component configuration would be straight forward extensions thereof and well-known to those skilled in the art made aware of this invention.

Synthetic Scheme for Polymer 5:

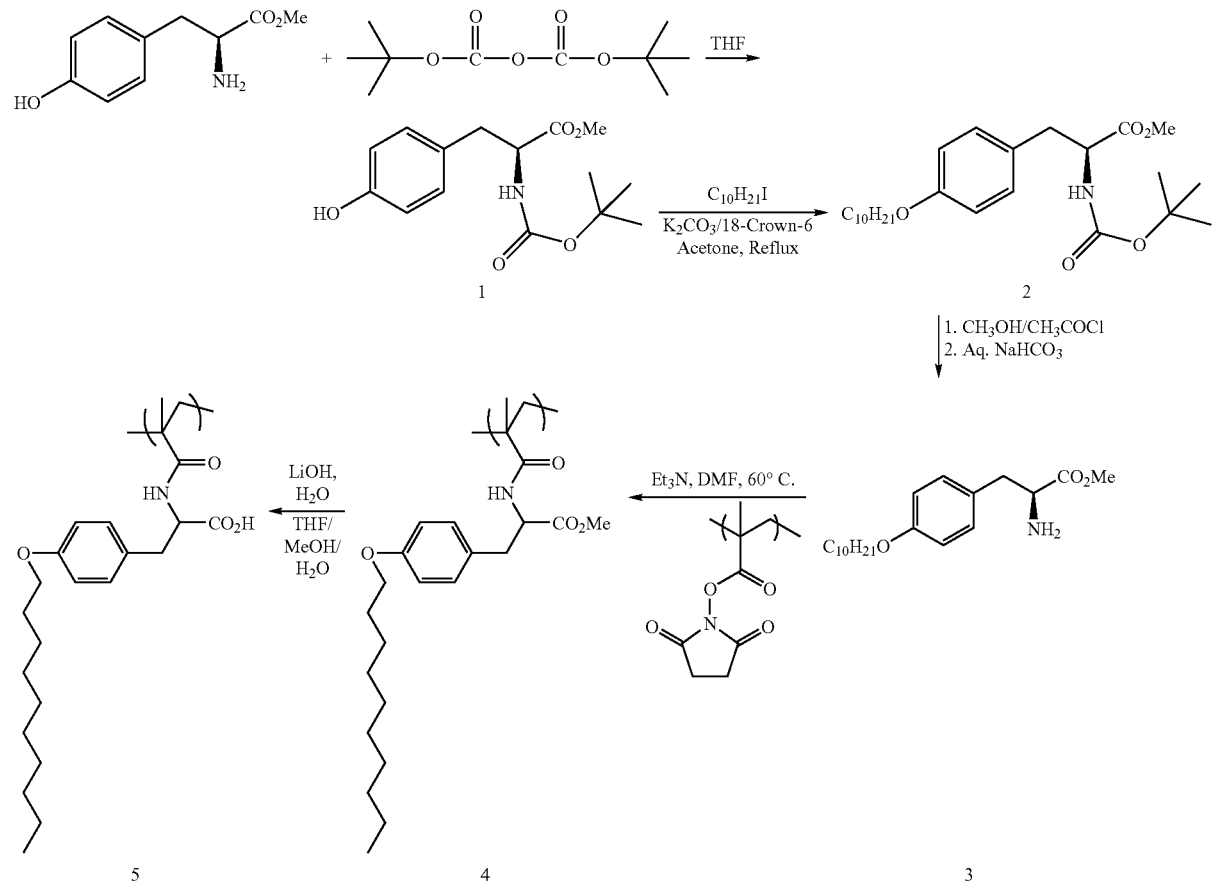

Example 8a

Preparation of Compound 1:

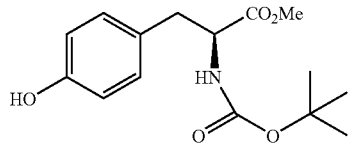

To a stirred solution of L-tyrosine methyl ester (2.2 g, 11.7 mmol) in dry THF (40 ml) was added di-tert-butyldicarbonate (2.7 g, 12.3 mmol) dissolved in dry THF (15 ml) dropwise for 10 min. The reaction mixture was stirred at room temperature for 14 h. The mixture was partitioned between water and EtoAc. The phases were separated, and the aqueous phase extracted with EtoAc. The combined organic layer was washed with brine solution and evaporated to dryness. The crude mixture was purified by silicagel column chromatograpy. Yield: 3.38 g (97%); $^1$HNMR (CDCl$_3$, 400 MHz) δ 6.96 (d, J=8.0 Hz, 2H), 6.74 (d, J=8.0 Hz, 2H), 6.65 (s, 1H), 5.09-5.07 (m, 1H), 4.56-4.54 (m, 1H), 3.72 (s, 3H), 3.05-2.98 (m, 2H), 1.43 (s, 9H); $^{13}$C NMR (CDCl$_3$, 100 MHz) δ 172.6, 155.3, 155.2, 130.2, 128.1, 115.4, 80.2, 54.5, 52.2, 37.5, 28.25.

Example 8b

Preparation of Compound 2:

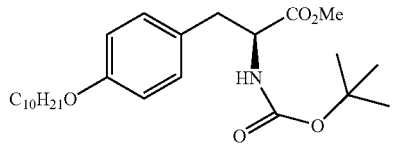

Compound 1 (3.3 g, 11.3 mmol) dissolved in acetone (50 ml). To this K$_2$CO$_3$ (1.8 g, 13.6 mmol), 18-Crown-6 (0.1 g, 0.6 mmol) and C$_{10}$H$_{21}$I (2.6 ml, 12.5 mmol) were added and heated to reflux for 12 h. The solvent was evaporated and the reaction mixture partitioned between water and dichloromethane. The phases were separated and the aqueous phase extracted with dichloromethane. The combined organic layer was washed with brine solution and evaporated to dryness. The crude mixture was purified by silicagel column chromatograpy. Yield: 4.5 g (93%); $^1$HNMR (CDCl$_3$, 400 MHz) δ 7.01 (d, J=8.8 Hz, 2ll), 6.81 (d, J=8.8 Hz, 2H), 4.95-4.93 (m, 1H), 4.55-4.51 (m, 1H), 3.91 (t, J=6.4 Hz, 2H), 3.71 (s, 3H), 3.03-3.00 (m, 2H), 1.79-1.27 (m, 25H), 0.88 (t, J=7.2 Hz, 3H).

Example 8c

Preparation of Compound 3:

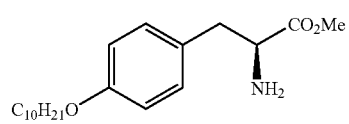

Acetyl chloride (4.8 ml, 67.3 mmol) was added dropwise to absolute methanol (75 ml) at 0° C. The compound 2 (2.9 g, 6.7 mmol) was added as a solid in one portion and the reaction mixture allowed to stir overnight at room temperature. Concentration of the reaction mixture gave 3 in hydrochloride salt, which was portioned between CH$_2$Cl$_2$ and saturated aqueous NaHCO$_3$. The phases were separated, and the aqueous phase was extracted with CH$_2$Cl$_2$. The combined organic phase was washed with brine solution and dried over MgSO$_4$. The solvent was evaporated to dryness to get the compound 3 as a white solid. Yield: 2.22 g (98%); $^1$H NMR (CDCl$_3$, 400 MHz) δ 7.1 (d, J=8.4 Hz, 2H), 6.85 (d, J=8.4 Hz, 2H), 3.94 (t, J=6.4 Hz, 2H), 3.73 (s, 3H), 3.72-3.69 (m, 1H), 3.06-3.01 (m, 1H), 2.85-2.80 (m, 1H), 1.80-1.29 (m, 16H), 0.90 (t, J=7.2 Hz, 3H); $^{13}$C NMR (CDCl$_3$, 100 MHz) δ 175.39, 157.95, 130.05, 128.72, 114.40, 67.80, 55.79, 51.75, 40.06, 31.76, 29.45, 29.42, 29.27, 29.18, 29.16, 25.92, 22.54, 13.98.

Example 8d

Polymer 4 and corresponding carboxylic acid 5 (n>1) can be prepared via amidation and basic hydrolysis.

Example 9

With reference to the following synthetic scheme, all reagents were commercially available and used as received unless stated otherwise. $^1$H-NMR spectra were recorded on a 400 MHz NMR spectrometer using residual proton resonance of the solvents as internal standard. Chemical shifts are reported in parts per million (ppm). $^{13}$C-NMR spectra were proton decoupled and recorded on a 100 MHz NMR spectrometer using the carbon signal of the deuterated solvent as the internal standard. Mass spectra were obtained at the Molecular Weight Characterization facility at University of Massachusetts. The molecular weights of the polymers were determined by size exclusion chromatography on a Waters single injector mode GPC, using THF as eluent and toluene as the internal reference; polystyrene standards were used for calibration and output was received and analyzed using a RI detector. The monomers were synthesized starting from 3,5-dihydroxybenzoic acid or 3,5-dihydroxybenzyl alcohol. All the compounds were characterized using $^1$H, $^{13}$C NMR and mass spectrometry. Reference numbers correspond only to the compounds shown and example 9. All the polymers, starting from C$_4$ (2f) to C$_{10}$ (5f) were synthesized from the compound 3,5-dihydroxybenzoic acid (1). The detailed synthetic procedure is given below.

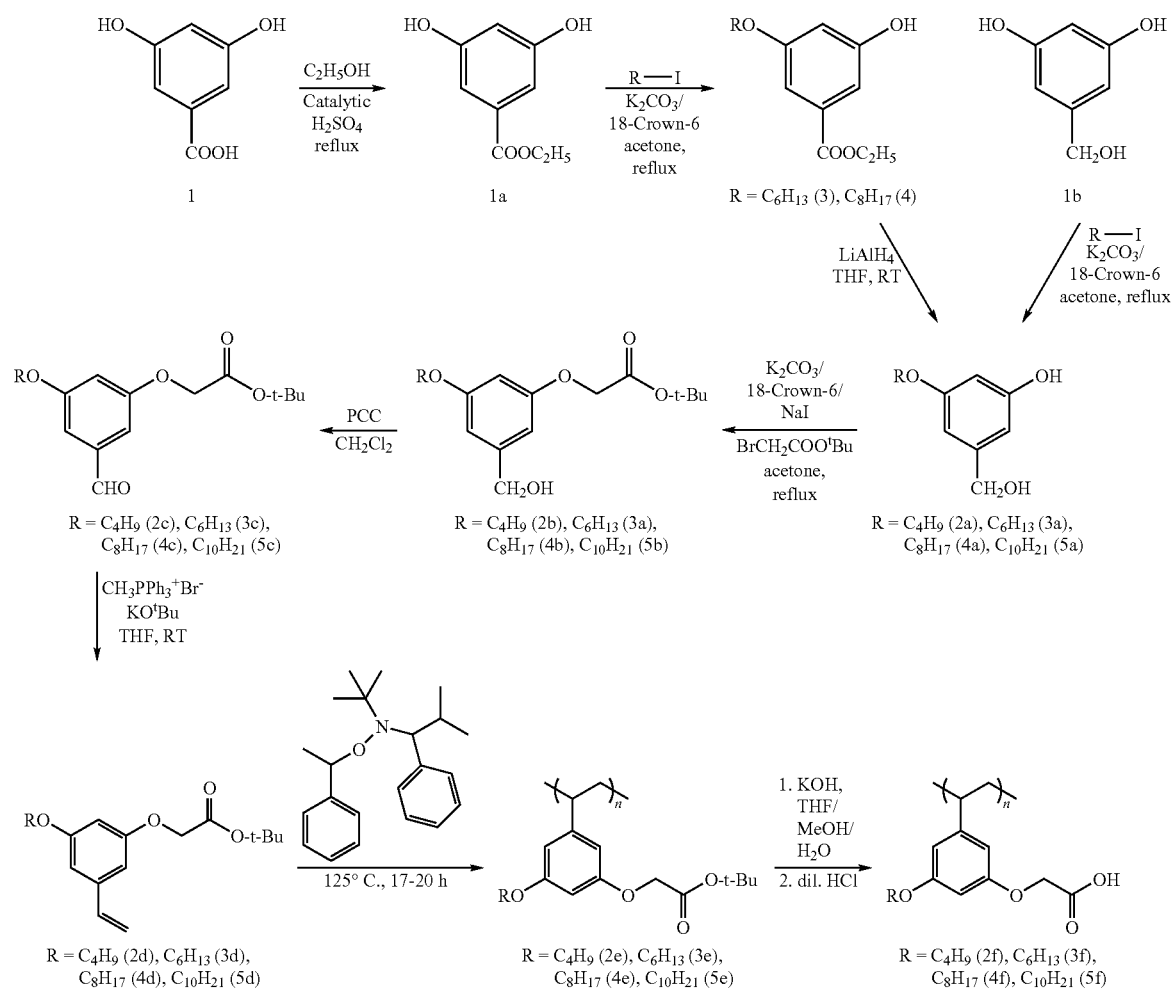

Example 9a

Synthesis of monomers was achieved from 3,5-dihydroxybenzoic acid or 3,5-dihydroxybenzyl alcohol as shown in above scheme. Commercially available 3,5-dihydroxybenzoic acid 1 was dissolved in ethanol along with catalytic amount of concentrated sulfuric acid and refluxed for 12 h to obtain ethyl-3,5-dihydroxybenzoate 1a. The ester 1a was then treated with one equivalent of alkyl halide to afford the mono alkylated ester 3 and 4. The yield of this reaction was rather low, because of the disubstituted byproduct obtained in the reaction along with the product as a statistical mixture. Compounds 3 and 4 were then reduced using $LiAlH_4$ in dry THF under ambient temperature to give the monoalkylated phenols 3a and 4a. Compounds 2a and 5a were prepared by the reaction of 3,5-dihydroxybenzyl alcohol with 1 equivalent of alkyl halide under alkylation conditions. The phenols 2a-5a were then treated with tert-butylbromoacetate and sodium iodide to give compounds 2b-5b, which upon oxidation by PCC afforded the corresponding aldehydes 2c-5c. Treatment of aldehydes with methyl triphenylphosphonium bromide and potassium tert-butoxide under THF afforded the monomers 2d-5d. Polymers 2e-5e (n>1) was synthesized by nitroxide mediated living polymerization, using unimolecular intiator. The polymers were then hydrolyzed using potassium hydroxide as the base to afford carboxylic acid polymers 2f-5f.

Example 9b

Synthesis of Compound (2a):

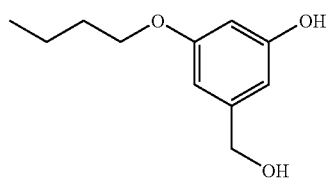

3,5-Dihydroxybenzyl alcohol 1b (21.2 g, 150 mmol) was dissolved in acetone (1000 mL). To this solution were added $K_2CO_3$ (42.0 g, 300 mmol) and 18-Crown-6 (4.0 g, 15 mmol) and stirred for 5 min. To this mixture, $C_4H_9I$ (17.5 mL, 150 mmol) was added and stirred to reflux for 20 h. The reaction mixture was then cooled to room temperature and the solvent was evaporated to dryness. To this residue, water and ethyl acetate were added and stirred for 30 min. The organic layer was separated and aqueous layer was extracted with ethyl acetate. The combined organic layer was washed with water and brine solution. The organic layer was evaporated to dryness and purified by silica gel column chromatography (40-45% ethyl acetate in hexanes) to afford 11.0 g (36% yield) of 2a. The major by-product of this reaction is the compound, where butyl groups are added to the two phenolic groups of compound 1b. $^1$H NMR (400 MHz, CDCl$_3$) δ 8.2 (s, 1H), 6.44 (s, 2H), 6.27 (t, J=2.0 Hz, 1H), 4.52 (s, 2H), 3.93 (t, J=6.6 Hz, 2H), 1.75-1.68 (quintet, 2H), 1.52-1.43 (quintet, 2H), 0.96 (t, J=7.4 Hz); $^{13}$C NMR (100 MHz, CDCl$_3$) δ 161.3, 159.2, 145.6, 106.5, 104.5, 101.1, 67.9, 64.6, 32.0, 19.8, 14.1; GC/MS (m/z, r.i): 196 (M$^+$, 52), 140 (100), 122 (15), 111 (32), 101 (15), 94 (10), 59 (30), 58 (8).

Example 9c

Synthesis of Compound (2b):

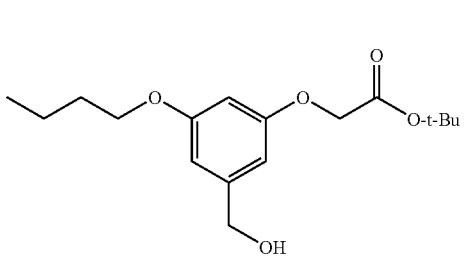

Compound 2a (8.0 g, 40.8 mmol) was dissolved in acetonitrile (75 mL). To this solution were added, K$_2$CO$_3$ (6.8 g, 49 mmol), NaI (6.72 g, 45 mmol) and 18-Crown-6 (0.65 g, 2.45 mmol) followed by tert-butyl bromoacetate (6.7 mL, 45 mmol). The reaction mixture was refluxed for 30 h. It was then cooled to room temperature and solvent was evaporated to dryness. The residue was partitioned between water and CH$_2$Cl$_2$. The organic layer was separated, and the aqueous layer was extracted with CH$_2$Cl$_2$. The combined organic layer was dried over Na$_2$SO$_4$ and evaporated to dryness. The crude product was purified by silica gel column chromatography (2-5% ethyl acetate in dichloromethane) to afford 10.8 g (85% yield) of 2b. $^1$H NMR (400 MHz, CDCl$_3$) δ 6.53 (s, 1H), 6.46 (s, 1H), 6.38 (t, J=2.4 Hz, 1H), 4.6 (s, 2H), 4.4 (s, 2H), 3.92 (t, J=6.6 Hz, 2H), 1.77-1.70 (quintet, 2H), 1.51-1.43 (m, 1H), 0.95 (t, J=7.4 Hz, 3H); $^{13}$C NMR (100 MHz, CDCl$_3$) δ 167.9, 160.3, 158.9, 143.4, 106.0, 104.5, 100.5, 82.2, 67.6, 65.5, 64.8, 31.1, 27.9, 19.0, 13.7; GC/MS (m/z, r.i): 310 (M$^+$, 100), 254 (72), 237 (10), 198 (98), 169 (15), 123 (14), 101 (8), 57 (76).

Example 9d

Synthesis of Compound (2c):

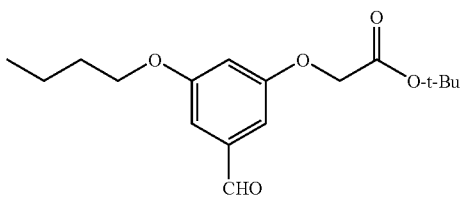

To a stirred solution of compound 2b (5.62 g, 18.2 mmol) in dry dichloromethane (125 mL) was added pyridinium chlorochromate (4.7 g, 21.8 mmol). It was stirred at room temperature for 3 h. The reaction mixture was filtered over alumina and the filtrate was evaporated and purified by silica gel column chromatography (8% ethyl acetate in hexanes) to afford 5.12 g (92% yield) of 2c. $^1$H NMR (400 MHz, CDCl$_3$) δ 9.88 (s, 1H), Hz, CDCl$_3$) δ 7.04 (s, 1H), 6.94 (s, 1H), 6.73 (t, J=2.4 Hz, 1H), 4.55 (s, 2H), 3.99 (t, J=6.6 Hz, 2H), 1.79-1.75 (quintet, 2H), 1.56-1.45 (m, 1H), 0.97 (t, J=7.4 Hz, 3H); $^{13}$C NMR (100 MHz, CDCl$_3$) δ 191.6, 167.4, 160.7, 159.4, 138.2, 109.0, 108.1, 106.6, 82.5, 68.1, 65.6, 31.0, 27.9, 19.0, 13.7; GC/MS (m/z, r.i): 308 (M$^+$, 98), 252 (55), 235 (22), 196 (95), 178 (10), 152 (15), 121 (14), 57 (100).

Example 9e

Synthesis of Compound (2d):

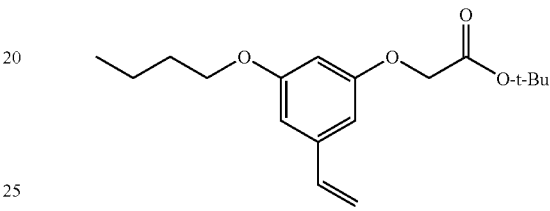

Commercially available CH$_3$PPh$_3$Br (7.5 g, 22 mmol) was taken in dry THF (150 mL) and KO$^t$Bu (2.36 g, 22 mmol) was added to this under argon atmosphere. This reaction mixture was stirred for 20 min and a solution of compound 2c (5.0 g, 16.3 mmol) in 100 mL of dry THF was added slowly using dropping funnel. The reaction mixture was further stirred at room temperature for 4 h. The reaction mixture was filtered and the filtrate evaporated and purified by silica gel column chromatography (2-3% ethyl acetate in hexanes) to afford 4.8 g (96% yield) of 2d. $^1$H NMR (400 MHz, CDCl$_3$) δ 6.64-6.58 (m, 2H), 6.52 (s, 1H), 6.39 (t, J=2.2 Hz, 1H), 5.69 (d, J=17.6 Hz, 1H), 5.23 (d, J=10.8 Hz, 1H), 4.49 (s, 2H), 3.94 (t, J=6.6 Hz, 2H), 1.76-1.73 (quintet, 2H), 1.50-1.45 (m, 11H), 0.96 (t, J=7.4 Hz, 3H); $^{13}$C NMR (100 MHz, CDCl$_3$) δ 167.8, 160.3, 159.0, 139.4, 136.6, 114.1, 106.0, 104.3, 101.0, 82.1, 67.6, 65.6, 31.1, 27.9, 19.1, 13.7.

Example 9f

Synthesis of Compound (2e):

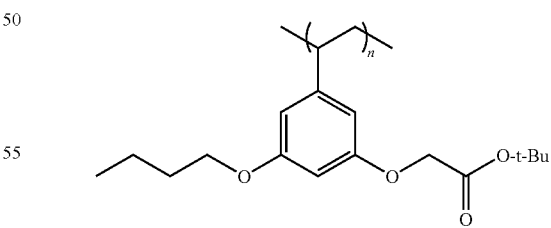

A mixture of the compound 2d (0.61 g, 2 mmol) and alkoxyamine (0.0065 g, 0.02 mmol) were degassed by three freeze/thaw cycles, sealed under argon, and heated at 125° C. under argon for 16 h. The reaction mixture was allowed to cool down to room temperature. The solidified reaction mixture was then dissolved in dichloromethane and precipitated into methanol/water mixture. The precipitate was then collected by vacuum filtration and dried to give the desired polystyrene, 2e, as a white solid (0.52 g, 85% yield); SEC (polystyrene/THF): $M_n$=22,666, $M_w$=29,086, PD=1.28; $^1$H-NMR (400 MHz, CDCl$_3$) δ 6.04-5.59 (m, 3H), 4.2 (s, 2H), 3.61 (s, 2H), 1.9-0.90 (m, 19H).

Example 9g

Synthesis of Compound (2f):

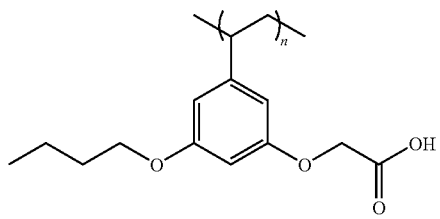

To a solution of polymer 2e ($M_n$=22,666, $M_w$=29,086, PD=1.28, 0.52 g, 1.71 mmol) in THF (18 mL) was added aqueous potassium hydroxide (0.96 g, 17.8 mmol) dissolved in water (3 mL). Methanol (9 mL) was then added to this two-phase system to give a homogeneous solution. This mixture was then heated at reflux for 12 h. The reaction mixture was evaporated to dryness and the residue redissolved in water (15 mL) and the mixture heated at reflux for another 24 h. After cooling to room temperature, the reaction mixture was acidified with 2N HCl. The precipitate formed was collected by vacuum filtration and dried to afford polymer 2f. Yield: 0.40 g (95%). $^1$H-NMR (400 MHz, DMSO-d$_6$) δ 12.9 (bs, 1H), 6.02-5.68 (m, 3H), 4.33 (s, 2H), 3.65 (s, 2H), 2.0-0.87 (m, 10M).

Example 9h

Synthesis of Compound (3):

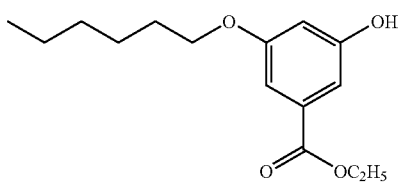

Ethyl-3,5-dihydroxybenzoate 1a (27.3 g, 150 mmol) was dissolved in acetone (750 mL). To this solution were added K$_2$CO$_3$ (20.7 g, 150 mmol) and 18-Crown-6 (1.9 g, 7.5 mmol) and stirred for 5 min. To this mixture, C$_6$H$_{13}$I (17.8 mL, 120 mmol) was added and stirred to reflux for 7 h. The reaction mixture was then cooled to room temperature and the solvent was evaporated to dryness. To this residue, water and ethyl acetate were added and stirred for 30 min. The organic layer was separated and aqueous layer was extracted with ethyl acetate. The combined organic layer was washed with water and brine solution. The organic layer was evaporated to dryness and purified by silica gel column chromatography (4% ethyl acetate in dichloromethane) to afford 13.5 g (34% yield) of 3. The major by-product of this reaction is the compound, where two hexyl groups are added to the two phenolic groups of compound 1. $^1$H NMR (400 MHz, CDCl$_3$) δ7.16 (s, 1H), 7.10 (s, 1H), 6.59 (t, J=2.2 Hz, 1H), 4.94 (s, 1H), 4.35 (q, J=7.2 Hz, 2H), 3.96 (t, J=6.6 Hz, 2H), 1.80-1.73 (quintet, 2H), 1.53-1.28 (m, 9H), 0.90 (t, J=7.0 Hz, 3H); $^{13}$C NMR (100 MHz, CDCl$_3$) δ 167.0, 160.3, 157.0, 132.0, 109.0, 107.7, 106.9, 68.3, 61.4, 31.5, 29.0, 25.6, 22.5, 14.1, 13.9; GC/MS (m/z, r.i): 266 (M$^+$, 50), 221 (15), 182 (100), 154 (20), 137 (30), 110 (15), 69 (11), 55 (8).

Example 9i

Synthesis of Compound (3a):

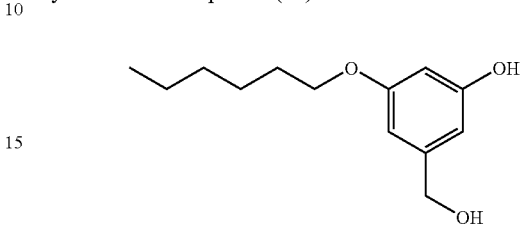

LiAlH$_4$ (2.6 g, 69 mmol) was taken in dry THF (150 mL) under argon atmosphere and cooled to 0° C. Compound 3 (12.2 g, 46 mmol) dissolved in dry THF (100 mL) was added dropwise to the above solution for 30 min. It was allowed to stir at room temperature for 12 h. The reaction mixture was quenched with ethyl acetate followed by water. The precipitated material was filtered and washed with ethyl acetate. The filtrate was then taken in a separating funnel. The organic layer was separated and the aqueous layer was extracted with ethyl acetate. The combined organic layer was washed with water, followed by brine solution. The organic layer was evaporated and purified by silica gel column chromatography (25-30% ethyl acetate in hexanes) to afford 8.4 g (82% yield) of 3a. $^1$H NMR (400 MHz, CDCl$_3$) δ 6.44 (s, 1H), 6.41 (s, 1H), 6.31 (t, J=2.0 Hz, 1H), 4.56 (s, 2H), 3.88 (t, J=6.6 Hz, 2H), 1.77-1.70 (quintet, 2H), 1.44-1.26 (m, 6H), 0.89 (t, J=6.8 Hz, 3H); $^{13}$C NMR (100 MHz, CDCl$_3$) δ 160.1, 157.0, 142.4, 106.3, 105.3, 101.1, 68.0, 64.5, 31.4, 29.0, 25.5, 22.4, 13.8; GC/MS (m/z, r.i): 224 (M$^+$, 30), 140 (100), 111 (25), 94 (6), 65 (5), 55 (8).

Example 9l

Synthesis of Compound (3b):

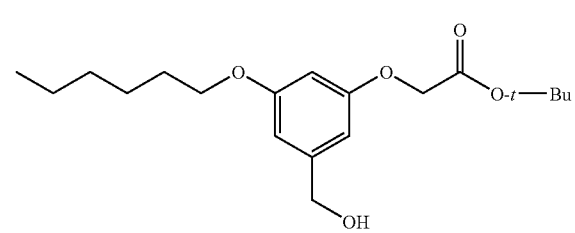

Compound 3a (12.3 g, 55 mmol) was dissolved in acetonitrile (150 mL). To this solution were added, K$_2$CO$_3$ (9.0 g, 65.5 mmol), NaI (9.8 g, 65.5 mmol) and 18-Crown-6 (0.73 g, 2.72 mmol) followed by tert-butyl bromoacetate (8.4 mL, 60 mmol). The reaction mixture was refluxed for 36 h. It was then cooled to room temperature and solvent was evaporated to dryness. The residue was partitioned between water and CH$_2$Cl$_2$. The organic layer was separated, and the aqueous layer was extracted with CH$_2$Cl$_2$. The combined organic layer was dried over Na$_2$SO$_4$ and evaporated to dryness. The crude product was dried under vacuum and taken into next step without further purification.

Example 9k

Synthesis of Compound (3c):

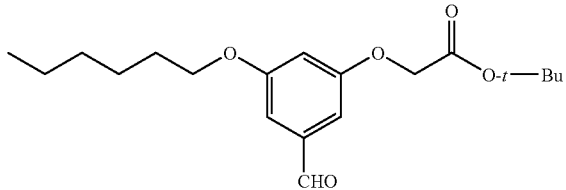

To a stirred solution of compound 3b (14.2 g, 41.9 mmol) in dry dichloromethane (290 mL) was added pyridinium chlorochromate (10.9 g, 50.3 mmol). It was stirred at room temperature for 4 h. The reaction mixture was filtered over alumina and the filtrate was evaporated and purified by silica gel column chromatography (8% ethyl acetate in hexanes) to afford 11.83 g (84% yield) of 3c. $^1$H NMR (400 MHz, CDCl$_3$) δ 9.88 (s, 1H), 7.03 (s, 1H), 6.94 (s, 1H), 6.73 (t, J=2.4 Hz, 1H), 4.55 (s, 2H), 3.98 (t, J=6.4 Hz, 2H), 1.83-1.76 (quintet, 2H), 1.49 (s, 9H), 1.45-1.33 (m, 6H), 0.90 (t, J=6.6 Hz, 3H); $^{13}$C NMR (100 MHz, CDCl$_3$) δ 191.3, 167.2, 160.5, 159.2, 138.1, 108.8, 107.8, 106.5, 82.3, 68.2, 65.4, 31.2, 28.7, 27.7, 25.4, 22.3, 13.7; GC/MS (m/z, r.i): 336 (M$^+$, 75), 280 (45), 263 (15), 235 (26), 196 (85), 152 (12), 121 (8).

Example 9l

Synthesis of Compound (3d):

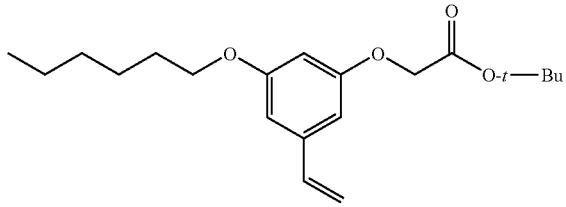

Commercially available CH$_3$PPh$_3$Br (16.0 g, 44 mmol) was taken in dry THF (150 mL) and KO$^t$Bu (5.0 g, 44 mmol) was added to this under nitrogen atmosphere. This reaction mixture was stirred for 20 min and a solution of compound 3c (11.8 g, 35.12 mmol) in 100 mL of dry THF was added slowly using dropping funnel. The reaction mixture was further stirred at room temperature for 5 h. The reaction mixture was filtered and the filtrate evaporated and purified by silica gel column chromatography (2-3% ethyl acetate in hexanes) to afford 10.0 g (85% yield) of 3d. $^1$H NMR (400 MHz, CDCl$_3$) δ 6.64-6.57 (m, 2H), 6.52 (s, 1H), 6.39 (t, J=2.2 Hz, 1H), 5.69 (d, J=17.6 Hz, 1H), 5.22 (d, J=10.8 Hz, 1H), 4.49 (s, 2H), 3.93 (t, J=6.6 Hz, 2H), 1.81-1.73 (quintet, 2H), 1.49 (s, 9H), 1.46-1.31 (m, 6H), 0.90 (t, J=6.6 Hz, 3H); $^{13}$C NMR (100 MHz, CDCl$_3$) δ 167.9, 160.3, 159.0, 139.5, 136.7, 114.2, 106.1, 104.3, 101.1, 82.2, 68.0, 65.7, 31.5, 29.1, 27.9, 25.6, 22.5, 13.9.

Example 9m

Synthesis of Compound (3e):

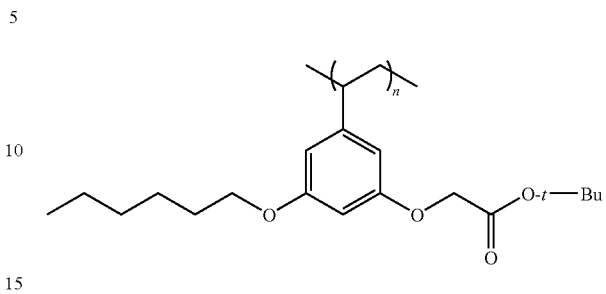

A mixture of the compound 3d (2.14 g, 6.41 mmol) and alkoxyamine (0.0139 g, 0.043 mmol) were degassed by three freeze/thaw cycles, sealed under argon, and heated at 125° C. under argon for 16 h. The reaction mixture was allowed to cool down to room temperature. The solidified reaction mixture was then dissolved in dichloromethane and precipitated into methanol/water mixture. The precipitate was then collected by vacuum filtration and dried to give the desired polystyrene, 3e, as a white solid (1.84 g, 86% yield); SEC (polystyrene/THF): $M_n$=29,900, $M_w$=37,600, PD=1.25; $^1$H-NMR (400 MHz, CDCl$_3$) δ 6.04-5.58 (m, 3H), 4.20 (s, 2H), 3.62 (s, 2H), 2.0-0.90 (m, 23H).

Example 9n

Synthesis of Compound (3f)

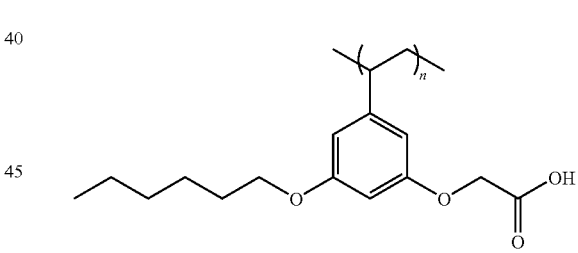

To a solution of polymer 3e ($M_n$=29,900, $M_w$=37,600, PD=1.25, 1.84 g, 5.51 mmol) in THF (72 mL) was added aqueous potassium hydroxide (3.6 g, 65 mmol) dissolved in water (12 mL). Methanol (30 mL) was then added to this two-phase system to give a homogeneous solution. This mixture was then heated at reflux for 12 h. The reaction mixture was evaporated to dryness and the residue redissolved in water (50 mL) and the mixture heated at reflux for another 24 h. After cooling to room temperature, the reaction mixture was acidified with 2N HCl. The precipitate formed was collected by vacuum filtration and dried to afford polymer 3f. Yield: 1.45 g (95%). $^1$H-NMR (400 MHz, DMSO-d$_6$) δ 12.9 (bs, 1H), 6.01-5.66 (m, 3H), 4.32 (s, 2H), 3.62 (s, 2H), 2.0-0.87 (m, 14H).

Example 9o

Synthesis of Compound (4):

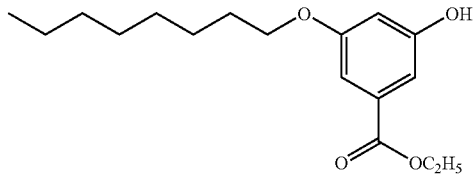

Ethyl-3,5-dihydroxybenzoate 1a (27.3 g, 150 mmol) was dissolved in acetone (750 mL). To this solution were added $K_2CO_3$ (20.7 g, 150 mmol) and 18-Crown-6 (1.9 g, 7.5 mmol) and stirred for 5 min. To this mixture, $C_8H_{17}I$ (21.7 mL, 120 mmol) was added and stirred to reflux for 7 h. The reaction mixture was then cooled to room temperature and the solvent was evaporated to dryness. To this residue, water and ethyl acetate were added and stirred for 30 min. The organic layer was separated and aqueous layer was extracted with ethyl acetate. The combined organic layer was washed with water and brine solution. The organic layer was evaporated to dryness and purified by silica gel column chromatography (3-4% ethyl acetate in dichloromethane) to afford 14.5 g (33% yield) of 4. The major by-product of this reaction is the compound, where two octyl groups are added to the two phenolic groups of compound 1a. $^1$H NMR (400 MHz, $CDCl_3$) δ 7.14 (s, 2H), 6.6 (t, J=2.2 Hz, 1H), 5.32 (s, 1H), 4.35 (q, J=7.2 Hz, 2H), 3.95 (t, J=6.6 Hz, 2H), 1.80-1.73 (quintet, 2H), 1.46-1.28 (m, 13H), 0.88 (t, J=6.8 Hz, 3H); $^{13}$C NMR (100 MHz, $CDCl_3$) δ 166.8, 160.3, 156.8, 132.0, 109.0, 107.8, 106.9, 68.3, 61.3, 31.7, 29.3, 29.2, 29.1, 25.9, 22.6, 14.2, 14.0; GC/MS (m/z, r.i): 294 ($M^+$, 68), 249 (12), 182 (100), 167 (8), 137 (25), 110 (12), 69 (12), 57 (8).

Example 9p

Synthesis of Compound (4a):

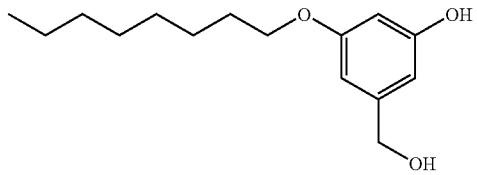

LiAlH (2.3 g, 60 mmol) was taken in dry THF (150 mL) and cooled to 0° C. Compound 4 (11.8 g, 40 mmol) was dissolved in dry THF (200 mL) was added dropwise to the above solution for 30 min. It was allowed to stir at room temperature for 12 h. The reaction mixture was quenched with ethyl acetate followed by water. The precipitated material was filtered and washed with ethyl acetate. The filtrate was then taken in a separating funnel. The organic layer was separated and the aqueous layer was extracted with ethyl acetate. The combined organic layer was washed with water, followed by brine solution. The organic layer was evaporated and purified by silica gel column chromatography (25-30% ethyl acetate in dichloromethane) to afford 9.43 g (94% yield) of 4a. $^1$H NMR (400 MH, $CDCl_3$) δ 6.5 (s, 1H), 6.4 (s, 1H), 6.32 (t, J=2.2 Hz, 1H), 4.61 (s, 2H), 3.93 (t, J=6.6 Hz, 2H), 1.80-1.72 (quintet, 2H), 1.47-1.28 (m, 10H), 0.89 (t, J=6.83H); $^{13}$C NMR (100 MHz, $CDCl_3$) δ 160.3, 157.1, 142.6, 106.3, 105.5, 101.2, 68.1, 64.9, 31.7, 29.3, 29.2, 29.1, 25.9, 22.6, 14.0; GC/MS (m/z, r.i): 252 ($M^+$, 70), 140 (100), 111 (30), 94 (6), 69 (10), 55 (10).

Example 9q

Synthesis of Compound (4b):

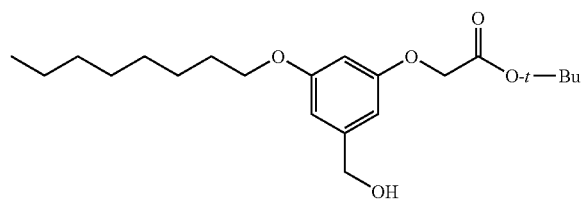

Compound 4a (12.0 g, 47.6 mmol) was dissolved in acetonitrile (150 mL). To this solution were added, $K_2CO_3$ (7.9 g, 57 mmol), NaI (7.13 g, 47.58 mmol) and 18-Crown-6 (0.75 g, 2.85 mmol) followed by tert-butyl bromoacetate (7.08 mL, 47.6 mmol). The reaction mixture was refluxed for 36 h. It was then cooled to room temperature and solvent was evaporated to dryness. The residue was partitioned between water and $CH_2Cl_2$. The organic layer was separated, and the aqueous layer was extracted with $CH_2Cl_2$. The combined organic layer was dried over $Na_2SO_4$ and evaporated to dryness. The crude product was purified by silica gel column chromatography (20% ethyl acetate in hexanes) to afford 16.7 g (95% yield) of 4b. $^1$H NMR (400 MHz, $CDCl_3$) δ 6.54 (s, 1H), 6.47 (s, 1H), 6.39 (t, J=2.4 Hz, 1H), 4.61 (s, 2H), 4.49 (s, 2H), 3.92 (t, J=6.6 Hz, 2H), 1.77-1.73 (quintet, 2H), 1.46 (s, 9H), 1.43-1.28 (m, 10H), 0.88 (t, J=7.0 Hz, 3H); $^{13}$C NMR (100 MHz, $CDCl_3$) δ 167.9, 160.2, 158.9, 143.4, 105.9, 104.5, 100.4, 82.2, 67.9, 65.4, 64.8, 31.6, 29.2, 29.1, 29.0, 27.8, 25.8, 22.5, 13.9; GC/MS (m/z, r.i): 366 ($M^+$, 95), 310 (52), 198 (100), 169 (8), 154 (9), 123 (5), 69 (14), 57 (55).

Example 9r

Synthesis of Compound (4c):

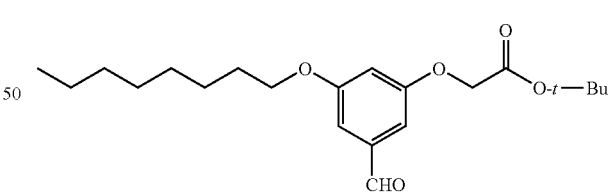

To a stirred solution of compound 4b (12.5 g, 34.2 mmol) in dry $CH_2Cl_2$ (230 mL) was added pyridinium chlorochromate (8.82 g, 41 mmol). It was stirred at room temperature for 4 h. The reaction mixture was filtered over alumina and the filtrate was evaporated and purified by silica gel column chromatography (8% ethyl acetate in hexanes) to afford 11.6 g (93% yield) of 4c. $^1$H NMR (400 MHz, $CDCl_3$) δ 9.88 (s, 1H), 7.03 (s, 1H), 6.94 (s, 1H), 6.73 (t, J=2.4 Hz, 1H), 4.55 (s, 2H), 3.97 (t, J=6.6 Hz, 2H), 1.81-1.74 (quintet, 2H), 1.49 (s, 9H), 1.45-1.28 (m, 10H), 0.88 (t, J=7.0 Hz, 3H); $^{13}$C NMR (100 MHz, $CDCl_3$) δ 191.4, 167.3, 160.6, 159.3, 138.1, 108.9, 107.9, 106.5, 82.4, 68.3, 65.5, 31.6, 29.1, 29.0, 28.9, 27.8, 25.8, 22.4, 13.9; GC/MS (m/z, r.i): 364 (M+, 70), 308 (40), 291 (15), 264 (15), 196 (69), 152 (11), 129 (8), 83 (10), 69 (32), 57 (100).

Example 9s

Synthesis of Compound (4d):

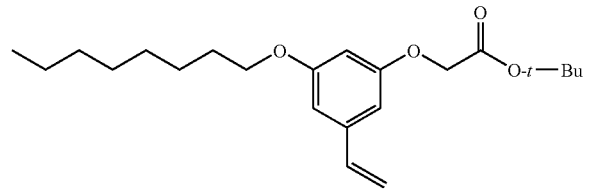

Commercially available CH$_3$PPh$_3$Br (14.4 g, 40.4 mmol) was taken in dry THF (150 mL) and KO$^t$Bu (4.52 g, 40.3 mmol) was added to this under nitrogen atmosphere. This reaction mixture was stirred for 20 min and a solution of compound 4c (11.3 g, 31.0 mmol) in 100 mL of dry THF was added slowly using dropping funnel. The reaction mixture was further stirred at room temperature for 5 h. The reaction mixture was filtered and the filtrate evaporated and purified by silica gel column chromatography (1-2% ethyl acetate in hexanes) to afford 10.2 g (91% yield) of 4d. $^1$H NMR (400 MHz, CDCl$_3$) δ 6.64-6.57 (m, 2H), 6.52 (s, 1H), 6.39 (t, J=2.2 Hz, 1H), 5.67 (d, J=17.6 Hz, 1H), 5.23 (d, J=10.8 Hz, 1H), 4.49 (s, 2H), 3.92 (t, J=6.6 Hz, 2H), 1.80-1.72 (quintet, 2H), 1.49 (s, 9H), 1.44-1.28 (m, 10H), 0.88 (t, J=6.8 Hz, 3H); $^{13}$C NMR (100 MHz, CDCl$_3$) δ 167.90, 160.3, 159.0, 139.5, 136.7, 114.2, 106.1, 104.3, 101.1, 82.2, 68.0, 65.7, 31.7, 29.2, 29.19, 29.17, 27.9, 25.9, 22.6, 14.0.

Example 9t

Synthesis of Compound (4e):

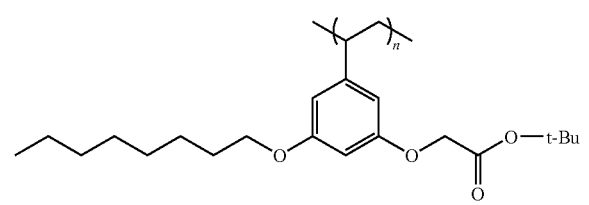

A mixture of the compound 4d (1.81 g, 5 mmol) and alkoxyamine (0.0162 g, 0.05 mmol) were degassed by three freeze/thaw cycles, sealed under argon, and heated at 125° C. under argon for 16 h. The reaction mixture was allowed to cool down to room temperature. The solidified reaction mixture was then dissolved in dichloromethane and precipitated into methanol/water mixture. The precipitate was then collected by vacuum filtration and dried to give the desired polystyrene, 4e, as a gummy product (1.75 g, 92% yield); SEC (polystyrene/THF): M$_n$=23,933, M$_w$=29,791, PD=1.24; $^1$H-NMR (400 MHz, DMSO-d$_6$) δ 6.05-5.56 (m, 3H), 4.67 (s, 2H), 3.95 (s, 2H), 1.57-0.86 (m, 27H).

Example 9u

Synthesis of Compound (4f):

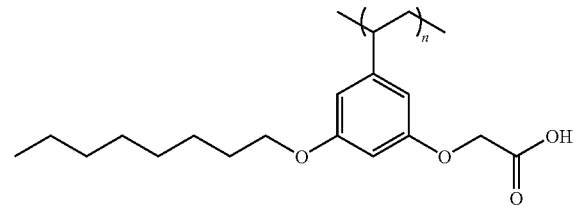

To a solution of polymer 4e (M$_n$=23,933, M$_w$=29,791, PD=1.24, 1.7 g, 4.7 mmol) in THF (54 mL) was added aqueous potassium hydroxide (2.8 g, 50 mmol) dissolved in water (9 mL). Methanol (22 mL) was then added to this two-phase system to give a homogeneous solution. This mixture was then heated at reflux for 12 h. The reaction mixture was evaporated to dryness and the residue redissolved in water (50 mL) and the mixture heated at reflux for another 24 h. After cooling to room temperature, the reaction mixture was acidified with 2N HCl. The precipitate formed was collected by vacuum filtration and dried to afford polymer 4f. Yield: 1.4 g (90%). $^1$H-NMR (400 MHz, DMSO-d$_6$) δ 13.0 (bs, 1H), 6.01-5.66 (m, 3H), 4.31 (s, 2H), 3.61 (s, 2H), 2.0-0.85 (m, 18H).

Example 9v

Synthesis of Compound (5a):

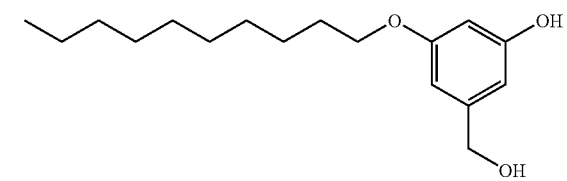

3,5-Dihydroxybenzyl alcohol 1b (21.0 g, 150 mmol), potassium carbonate (20.7 g, 150 mmol), 18-Crown-6 (2.0 g, 7.5 mmol) and C$_{10}$H$_{21}$I (32 mL, 150 mmol) were taken in 750 mL of acetone and refluxed for 12 h under argon atmosphere. The reaction mixture was allowed to cool and solvent was evaporated to dryness. The residue was partitioned between water and ethyl acetate. The organic layer was separated, the aqueous layer extracted with ethyl acetate. The combined organic layer was washed with brine and dried with anhydrous Na$_2$SO$_4$ and evaporated to dryness. The residue was purified by silica gel column, eluting with EtOAc/hexane (40:60) to afford 13.0 g (31%) of 5a as a colorless solid. $^1$H-NMR (400 MHz, CDCl$_3$) δ 6.48 (s, 1H), 6.43 (s, 1H), 6.32 (t, J=2.0 Hz, 1H), 4.60 (s, 2H), 3.92 (t, J=6.4 Hz, 2H), 1.79-1.72 (quin, 2H), 1.45-1.27 (m, 14H), 0.88 (t, J=6.6 Hz, 3H); $^{13}$C-NMR (100 MHz, CDCl$_3$) δ 160.4, 157.1, 142.7, 106.2, 105.4, 101.2, 68.1, 64.9, 31.8, 29.57, 29.41, 29.31, 29.19, 25.9, 22.6, 14.0; EI/MS (m/z, r.i): 280 (M+, 55), 140 (100), 111 (12), 57 (8).

Example 9w

Synthesis of Compound (5b):

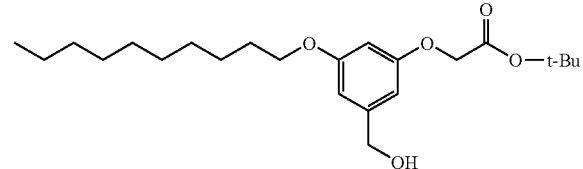

Compound 5a (11.53 g, 41.1 mmol) was dissolved in acetonitrile (125 mL). To this solution were added, $K_2CO_3$ (6.8 g, 49.3 mmol), NaI (6.16 g, 41.1 mmol) and 18-Crown-6 (0.52 g, 2.0 mmol) followed by tert-butyl bromoacetate (6.0 mL, 41.1 mmol). The reaction mixture was refluxed for 36 h. It was then cooled to room temperature and solvent was evaporated to dryness. The residue was partitioned between water and $CH_2Cl_2$. The organic layer was separated, and the aqueous layer was extracted with $CH_2Cl_2$. The combined organic layer was dried over $Na_2SO_4$ and evaporated to dryness. The crude product was purified by silica gel chromatography by elution with EtOAc/hexane (20:80) to afford 15.9 g of compound 5b (98% yield). $^1$H-NMR (400 MHz, $CDCl_3$) δ 6.54 (s, 1H), 6.47 (s, 1H), 6.39 (t, J=2.2 Hz, 1H), 4.61 (s, 2H), 4.49 (s, 2H), 3.92 (t, J=6.4 Hz, 2H), 1.79-1.72 (quin, 2H), 1.49 (s, 9H), 1.44-1.27 (m, 14H), 0.88 (t, J=6.8 Hz, 3H); $^{13}$C-NMR (100 MHz, $CDCl_3$) δ 167.9, 160.3, 159.0, 143.4, 106.0, 104.5, 100.5, 82.2, 67.9, 65.5, 64.9, 31.7, 29.48, 29.46, 29.28, 29.22, 29.10, 27.9, 25.9, 22.5, 14.0; GC/MS (m/z, r.i): 394 ($M^+$, 100), 338 (50), 198 (75), 83 (32), 57 (35).

Example 9x

Synthesis of Compound (5c):

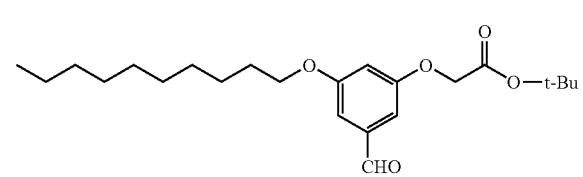

To a stirred solution of compound 5b (9.8 g, 24.9 mmol) in dry $CH_2Cl_2$ (180 mL) was added pyridinium chlorochromate (6.46 g, 30 mmol). It was stirred at room temperature for 3 h. The reaction mixture was filtered over alumina and the filtrate was evaporated and purified by silica gel column chromatography (12-15% ethyl acetate in hexanes) to afford 8.43 g (87% yield) of 5c. $^1$H NMR (400 MHz, $CDCl_3$) δ 9.89 9s, 1H), 7.03 (s, 1H), 6.94 (s, 1H), 6.73 (t, J=2.2 Hz, 1H), 4.55 (s, 2H), 3.97 (t, J=6.4 Hz, 2H), 1.80-1.74 (quintet, 2H), 1.49 (s, 9H), 1.45-1.27 (m, 14H), 0.88 (t, J=6.6 Hz, 3H); $^{13}$C NMR (100 MHz, $CDCl_3$) δ 191.5, 167.3, 160.6, 159.3, 138.2, 109.0, 108.0, 106.5, 82.4, 68.3, 65.5, 31.7, 29.44, 29.42, 29.2, 29.1, 28.9, 27.8, 25.8, 22.5, 13.9; GC/MS (m/z, r.i): 392 (Mt, 100), 336 (58), 292 (15), 196 (80), 152 (15), 83 (6), 57 (92).

Example 9v

Synthesis of Compound (5d):

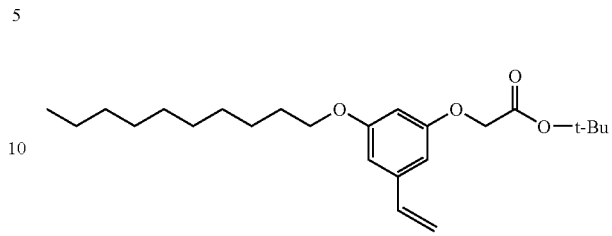

Commercially available $CH_3PPh_3Br$ (10 g, 28 mmol) was taken in dry THF (200 mL) and KO$^t$Bu (3.2 g, 28 mmol) was added to this under nitrogen atmosphere. This reaction mixture was stirred for 20 min and a solution of compound 5c (8.5 g, 22 mmol) in 150 mL of dry THF was added slowly from a dropping funnel. The reaction mixture was further stirred at room temperature for 5 h. The reaction mixture was filtered and the filtrate evaporated and purified by silica gel column chromatography (1-2% ethyl acetate in hexanes) to afford 7.7 g (92% yield) of 5d. $^1$H NMR (400 MHz, $CDCl_3$) 6.65-6.58 (m, 2H), 6.53 (s, 1H), 6.39 (t, J=2.2 Hz, 1H), 5.70 (d, J=17.6 Hz, 1H), 5.23 (d, J=10.8 Hz, 1H), 4.50 (s, 2H), 3.93 (t, J=6.6 Hz, 2H), 1.80-1.74 (quintet, 2H), 1.49 (s, 9H), 1.46-1.28 (m, 14H), 0.88 (t, J=6.8 Hz, 3H); $^{13}$C NMR (100 MHz, $CDCl_3$) δ 167.8, 160.3, 159.0, 139.5, 136.7, 114.2, 106.1, 104.3, 101.1, 82.2, 68.0, 65.6, 31.8, 29.52, 29.50, 29.3, 29.2, 29.1, 27.9, 22.6, 14.0.

Example 9z

Synthesis of Compound (5e):

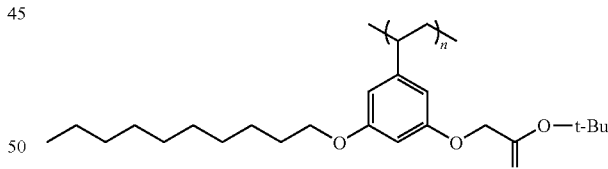

A mixture of the compound 5d (1.17 g, 3 mmol), alkoxyamine (0.0097 g, 0.03 mmol) were degassed by three freeze/thaw cycles, sealed under argon, and heated at 125° C. under argon for 24 h. The reaction mixture was allowed to cool down to room temperature. The solidified reaction mixture was then dissolved in dichloromethane and precipitated into methanol/water mixture. The precipitate was then collected by vacuum filtration and dried to give the desired polystyrene, 5e, as a gummy product 1.1 g (90% yield); SEC (polystyrene/THF): $M_n$=19621, $M_w$=24,430, PD=1.24; $^1$H-NMR (400 MHz, $CDCl_3$) δ 6.04-5.71 (m, 3H), 4.52 9s, 2H), 3.95 (s, 2H), 2.0-0.91 (m, 311).

Example 9aa

Synthesis of Compound (5f):

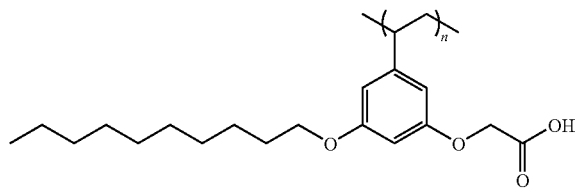

To a solution of polymer 5e ($M_n$=19621, $M_w$=24,430, PD=1.24, 1.1 g, 2.82 mmol) in THF (32 mL) was added aqueous potassium hydroxide (1.68 g, 30 mmol) dissolved in water (5 mL). Methanol (15 mL) was then added to this two-phase system to give a homogeneous solution. This mixture was then heated at reflux for 12 h. The reaction mixture was evaporated to dryness and the residue redissolved in water (20 mL) and the mixture heated at reflux for another 24 h. After cooling to room temperature, the reaction mixture was acidified with 2N HCl. The precipitate formed was collected by vacuum filtration and dried to afford polymer 5f. Yield: 0.95 g (89%). $^1$H-NMR (400 MHz, DMSO-$d_6$) δ 12.9 (bs, 1H), 6.01-5.66 (m, 3H), 4.33 (s, 2H), 3.60 (s, 2H), 2.0-0.86 (m, 22H).

Example 10

As shown above, amphiphilic homopolymers 2f-5f, of example 9, were synthesized by free radical polymerization. Though initially it showed high polydispersity index, the PDI can, optionally, be controlled by atom transfer-radical polymerization (ATRP), techniques known in the art.

To prepare the micelle like assemblies, the polymers of 2f-5f were dissolved in polar solvent, for example, water. Typically, the polymers are taken in a measured quantity, and then 1-1.5 equivalents of base was added to it, in order to convert the water insoluble POOH groups into water insoluble —COO$^-$ group. These rendered the amphiphilic homopolymers soluble in water. After adding the base to water solution of the polymer, it was heated up to ~40 degrees, and sonicated for 3 hours, to obtain an optically clear solution. The UV-Vis spectra of these solutions, confirmed the presence of the polymer in the water layer. Different dyes were then added to the polymer solution. The dyes chosen are hydrophobic, insoluble or sparingly soluble in water, to demonstrate such compounds can be encapsulated inside a nanostructure/assembly, formed by the polymeric micelles.

To the optically clear solution of the micelles, Reichardt's Dye, Pyrene and Orange-OT dyes were added. The micellar solution of the polymers were then sonicated for ~3 more hours at ~40 degrees, to ensure the solubility of the dyes inside the micelles. After the sonication, the solutions were filtered, and stored in a vial and the UV-Vis spectra of the polymers were taken. Representative results are summarized below.

Example 10a

Solvatochromic and water insoluble Reichardt's dye was encapsulated in the decyl polymer (5f). Spectra show the concentration dependence of the polymer solution, where $10^{-4}$ M polymer solution encapsulates more dye than $10^{-5}$ or $10^{-6}$ M. Similar trends are seen for the dye Orange OT, encapsulated in the micelle solution of the $C_{10}$ polymer.

Example 10b

The same dyes employed above were encapsulated inside the nanoassembly formed by the $C_8$ polymers (4f). A similar concentration dependent trend was also seen here.

Example 10c

Similar studies were conducted using the benzyl polymer of example 3a, FIG. 1. Here also the interior of the polymeric micelle is hydrophobic enough to encapsulate the dyes.

Example 10d

Encapsulation of hydrophobic Reichardt's dye by the $C_6$ polymer (3f) showed similar concentration trends.

Example 10e

Encapsulation of Reichardt's dye and Orange OT, respectively, in water by the $C_4$ polymer (2f) showed similar concentration trends.

Example 11

After confirming that the polymers form hydrophobic assemblies in a polar solvent like water, the polarity of the interior of the micelles was studied via fluorescence spectrometry by encapsulating Pyrene inside the assembled nanocontainer and then calculating its $I_1$ and $I_3$ ratio. If the polarity of the microenvironment is more like water, it was believed this ratio would be about 1.8 and if it is non polar, the ratio will close to 1 or less.

Summarizing Data and Intensity Ratios at Representative Concentrations:

| Polymer Chain length | $I_1/I_3$ ($10^{-4}$ M) | $I_1/I_3$ ($10^{-8}$ M) |
|---|---|---|
| $C_4$ (2f) | 1.03 | 1.65 |
| $C_6$ (3f) | 0.89 | 1.77 |
| Benzyl (3a, FIG. 1) | 1.12 | 1.46 |
| $C_8$ (4f) | 0.74 | 1.53 |
| $C_{10}$ (5f) | 0.74 | 1.39 |

The data shows that, with increasing chain length, the hydrophilicity of the micellar interior decreases, supporting formation of micellar structure.

Example 12

Critical micelle concentration can be employed in determining the micellar characteristics of different systems. Using Pyrene excitation spectra ($I_{338}/I_{333}$) CMC values were found for the $C_4$ (2f) polymer: 2.05×$10^{-6}$M; the $C_6$ (3f) polymer: 2.28×$10^{-7}$M; the $C_8$ (4f) polymer: 3.89×$10^{-7}$M; and the $C_{10}$ (5f) polymer: 5.54×$10^{-7}$M.

Example 13

As a companion study, in comparison with the results of example 10, UV-Vis spectra wave obtained for various polymer concentrations ($10^{-4}$, $10^{-5}$ and $10^{-6}$ M) encapsulating several water-soluble dyes in toluene. The results demonstrate inversion of the amphiphilic polymers of this invention and corresponding micellar assembly.

The UV-Vis spectra of water-soluble dyes (e.g., rhodamine 6G and proflavine) in toluene, in presence of $C_6$, $C_8$ and $C_{10}$ show a concentration dependence; a higher concentration of the polymers show higher amount of dye encapsulated.

Example 14

Extending the results of the previous examples, encapsulated dyes can be released upon change and solvent environment. As demonstrated below, for a particular dye and amphiphilic polymer, /phase transfer is observed to create such results are indicative of the release and delivery properties of this invention, as can be utilized in conjunction with various other components including but not limited to various therapeutic agents as would be understood by those skilled in the art made aware of this invention.

Example 14a

Reichardt's dye was taken up in $10^{-4}$M $C_{10}$ polymer and water, providing a greenish-blue color, over a dichloromethane (DCM) layer. After shaking for ten seconds, the DCM layer slowing turned blue, with the aqueous layer becoming less intense in color. After five minutes, the DCM layer was a deep blue color, with the aqueous layer colorless. Such results demonstrate the dye was easily released from the polymeric structure, and phase transfer was almost quantitative.

Example 14b

Rhodamine 6G was taken up in $10^{-4}$M $C_{10}$ polymer in DCM. The solution was red in color. Water was added to the system, providing a lower layer. After shaking for 10 seconds, no color/phase transfer was observed, even upon addition of urea and additional shaking (40 seconds). After 24 hours. no color change was observed, with the dye remaining in the toluene layer. Such results indicate the hydrophilic dye is strongly bound to the inverted micelle assembly, prohibiting release to even a favorable water solvent.

To confirm the preceding, the $C_{10}$ polymer ($10^{-4}$M was taken in toluene (colorless) and allowed to equilibrate with rhodamine 6G in water (orange solution). After shaking for ten seconds, the upper toluene layer became slightly red in color. After shaking for 40 seconds, the upper layer became even more intense in color, with the lower equis becoming less intense in color. After five minutes, the aqueous layer was completely colorless, and the toluene layer was a deep orange color. Such results show that the rhodamine 6G was transferred (extracted) readily from the aqueous phase to polymeric assemblies in the organic phase.

Example 14c

A water-soluble dye rose bengal was taken up in $10^{-4}$M $C_{10}$ polymer in toluene (red colored solution), with a lower water phase introduced thereto. After shaking for 40 seconds, the water layer started to acquire a red color, with the toluene layer becoming less intense in color. After 24 hours, the toluene layer was completely colorless, with the water layer intensely red in color, indicating complete transfer of dye from the organic to aqueous phase. Such results indicate that rose bengal dye is less strongly bound to the $C_{10}$ polymer assembly, as compared to rhodamine G6 of the previous examples, allowing eventual release and phase transfer.

Conversely, rose bengal dye was dissolved in water and contacted with a toluene phase containing the $C_{10}$ polymer: no dye was transferred from the aqueous to the organic phase, consistent with the preceding results.

Example 14d

Rose bengal and rhodamine G6 were contacted with $C_{10}$ polymer ($10^{-4}$M) and toluene, providing a solution deep red in color. An aqueous phase was introduced, and after approximately one minute of shaking, the aqueous phase started to acquire a red color, but the toluene layer was not observed to lose intensity. Further analysis showed the rose bengal dye was transferred to the aqueous phase, while the rhodamine 6G dye remained in the organic phase. Such results indicate a micellar system of this invention can be used to separate a mixture of compounds.

Example 15

Upon demonstrating micelle and inverted micelle like polymer assemblies through design at monomer level, a similar principle was employed to provide vestical structures: two hydrophilic groups attached to the same monomer unit, coupled one to another via a long hydrophobic chain.

Accordingly, three representative polymers, designated 60a, 60b and 60c were designed (m>1), as shown below, prepared from the corresponding monomeric (58) and polymeric (59) esters. These three vary in chain length of the hydrophobic part.

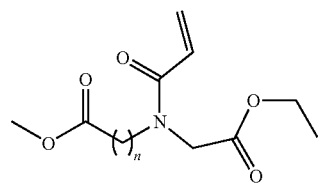

58a: n = 10
58b: n = 05
58c: n = 15

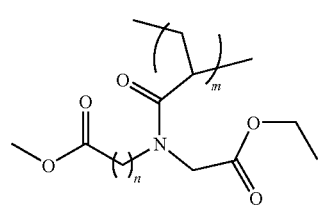

59a: n = 10, Mn = 28K, PDI = 1.32
59b: n = 05, Mn = 24K, PDI = 1.30
59c: n = 15, Mn = 30K, PDI = 1.36

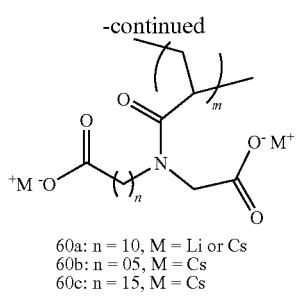

60a: n = 10, M = Li or Cs
60b: n = 05, M = Cs
60c: n = 15, M = Cs

TEM micrographs show vesicle formation in an aqueous phase, with inversion in an organic phase (e.g., toluene).

With respect to example 15, $^1$H-NMR spectra were recorded on a 400 MHz NMR spectrometer using the residual proton resonance of the solvent as the internal standard. Chemical shifts are reported in parts per million (ppm). When peak multiplicities are given, the following abbreviations are used: s, singlet; d, doublet; t, triplet; q, quartet; quin, quintet; m, multiplet; b, broad.

$^{13}$C-NMR spectra were proton decoupled and recorded on a 100 MHz NMR spectrometer using the carbon signal of the deuterated solvent as the internal standard. EI mass spectra were obtained at the Coordinated Instrumentation Facility at University of Massachusetts. Flash chromatography was performed with 37-75 μm silica gel. Analytical thin layer chromatography was performed on silica plates with F-254 indicator and the visualization was accomplished by UV lamp or using an iodine chamber. THF and toluene were distilled over Na/Ph$_2$CO. All other chemicals were obtained from commercial sources and used as received, unless otherwise mentioned.

Example 15a

General Procedure for the Esterification of Bromoalkanoic Acids (I):

Appropriate bromo alkanoic acid (1 equiv) was dissolved in methanol and a catalytic amount of conc.H$_2$SO$_4$ (0.1 mL/g) was added and the reaction mixture was refluxed for overnight. Upon reaction completion, methanol was removed in rotary evaporation and the crude product was washed with aq. NaHCO$_3$, brine solution and extracted with ethyl acetate. The product was used further without column purification.

Example 15b

General Procedure for Amine Alkylation (II):

Glycine ethyl ester hydrochloride (2 equiv), triethylamine (4 equiv), and the appropriate aliphatic methyl bromoacetate (1 equiv) were mixed together in ethanol and the reaction mixture was refluxed for 24 h under argon atmosphere. After the solvent removal, the residue was dissolved in water and extracted using dichloromethane. Solvent was removed and the crude reaction mixture was purified through silica-gel column chromatography to get the monoalkylated glycine ester.

Example 15c

General Procedure for the Synthesis of Acrylate Monomer (III):

Appropriate monoalkylated glycine ethyl ester (1 equiv), triethylamine (1.2-1.3 equiv), and small amount of p-methoxy phenol were mixed together in dry dichloromethane under argon atmosphere and the mixture was stirred at 40° C. Acryloyl chloride (1.3-1.4 equiv) was added drop wise to the reaction mixture and the stirring was continued for 6 h. Then the crude reaction mixture was washed with 1N HCl, saturated NaHCO$_3$ and brine solution. Solvent was removed from the reaction mixture, and the acrylate monomer was purified using silica gel column chromatography with ethyl acetate/hexane as the eluent.

Example 15d

Synthesis of Methyl 6-Bromohexanoate (11):

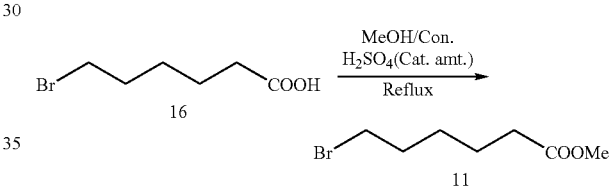

As mentioned in the general procedure (I), 6-bromohexanoic acid (15 g, 76.9 mmol, 1 equiv) was dissolved in methanol (150 mL), and a catalytic amount of conc.H$_2$SO$_4$ (2 mL) was added and the reaction was carried out. The product was taken to next step without column purification. Yield 14.8 g (92%). $^1$H NMR (400 MHz, CDCl$_3$): δ 3.66 (s, 3H), 3.42-3.38 (m, 2H), 2.32 (t, J=7.2 Hz, 2H), 1.90-1.83 (m, 2H), 1.68-1.61 (m, 2H), 1.50-1.44 (m, 2H). $^{13}$C NMR (100 MHz, CDCl$_3$); δ 173.9, 51.5, 33.8, 33.4, 32.3, 27.6, 24.0. EI/MS m/z (r.i.) 211(M+2, 98), 210(M+1, 8), 209(M+, 100), 178(16), 161 (33), 129(51), 97(28), 87(9), 74(23), 69(23).

Example 15e

Synthesis of Methyl 16-Bromo Hexadecanoate (12):

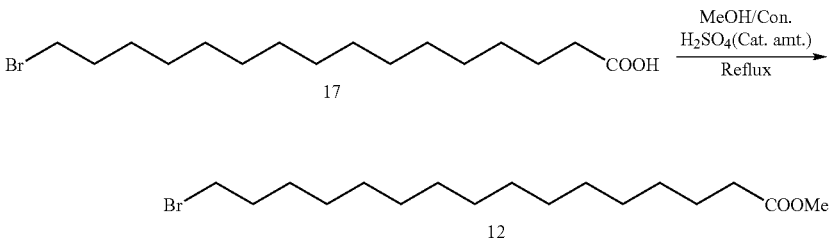

As mentioned in the general procedure (1), 16-bromohexadecanoic acid (5 g, 14.9 mmol, 1 equiv) was dissolved in methanol (50 mL), and a catalytic amount of conc.$H_2SO_4$ (1 mL) was added and the reaction was carried out. The product was used further without column purification. Yield 4.68 g (90%). $^1$H NMR (400 MHz, $CDCl_3$): δ 3.66 (S, 3H), 3.40 (t, J=6.8 Hz, 2H), 2.29 (t, J=7.2 Hz, 2H), 1.84 (quin, J=7.2 Hz, 2H), 1.61 (m, 2H), 1.41 (m, 2H), 1.27 (m, 20H). $^{13}$C NMR (100 MHz, $CDCl_3$); δ 174.3, 51.4, 34.1, 34.0, 32.8, 29.6, 29.5, 29.4, 29.2, 29.1, 28.7, 28.1, 24.9. EI/MS m/z (r.i.) 350(M+2, 34), 349(M+1, 8), 348(M+, 35), 319(9), 269(35), 143(16), 129(8), 87(60), 74(100), 55(26).

Example 15f

Compound 13:

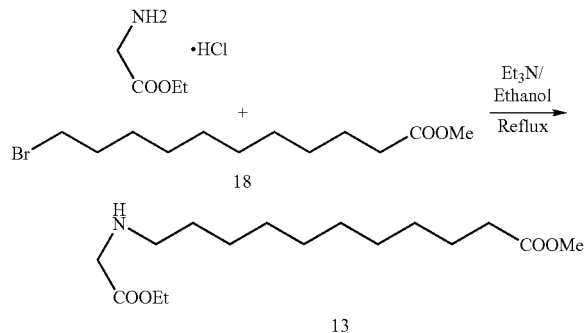

According to the general procedure (11), glycine ethyl ester hydrochloride (10 g, 71.6 mmol, 2 equiv), triethylamine (20 mL, 143.2 mmol, 4 equiv), and methyl 11-bromoundecanoate (10 g, 35.8 mmol, 1 equiv) were mixed together in ethanol and reacted. Solvent was removed and the crude reaction mixture was purified through silica-gel column chromatography by using methanol/ethyl acetate (2:98) as the eluent to get the monosubstituted glycine ester (13). Yield 4.53 g (42%). $^1$H NMR (400 MHz, $CDCl_3$): δ 4.14 (q, J=7.2 Hz, 2H), 3.61 (s, 3H), 3.34 (s, 2H), 2.53 (t, J=7.2 Hz, 2H), 2.24 (t, J=7.2 Hz, 2H), 1.71 (s, 1H), 1.57-1.52 (m, 2H), 1.44-1.39 (m, 2H), 1.24-1.20 (m, 15H). $^{13}$C NMR (100 MHz, $CDCl_3$); δ 174.3, 172.5, 60.6, 51.5, 51.4, 51.3, 51.2, 50.9, 50.8, 49.6, 34.0, 29.9, 29.4, 29.3, 29.1, 29.0, 27.1, 24.8, 14.1. EI/MS m/z (r.i.) 303 (M+2, 5), 302(M+1, 19), 301(M+, 100), 270(5), 228(46), 196(5), 116(19), 84(8), 55(5).

Example 15g

Compound 14:

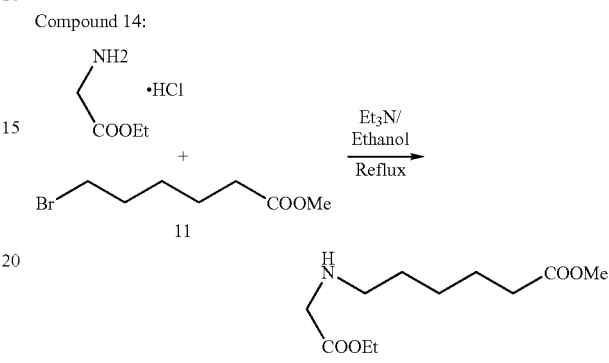

As per the general procedure (II), glycine ethyl ester hydrochloride (21.4 g, 153 mmol, 2 equiv), triethylamine (42.7 mL, 306 mmol, 4 equiv), and methyl 6-bromohexanoate (16 g, 76.5 mmol, 1 equiv) were mixed together in ethanol and reacted. Solvent was removed and the crude reaction mixture was purified through silica-gel column chromatography by using methanol/ethyl acetate (3:97) as the eluent to get the monoalkylated glycine ester (14). Yield 9.2 g (52%).

$^1$H NMR (400 MHz, $CDCl_3$): δ 4.21-4.15 (m, 2H), 3.66 (S, 3H), 3.41-3.40 (m, 2H), 2.64-2.61 (m, 2H), 2.30 (t, J=7.2 Hz, 2H), 1.67-1.59 (m, 2H), 1.55-1.51 (m, 2H), 1.40-1.32 (m, 2H), 1.26 (t, J=7.2 Hz, 3H). $^{13}$C NMR (100 MHz, $CDCl_3$); δ 174.0, 172.2, 60.6, 51.4, 50.7, 49.2, 33.8, 29.5, 26.6, 24.6, 14.1. EI/MS m/z (r.i.) 233(M+2, 5), 232(M+1, 13), 231(M+, 7), 200(5), 185(5), 158(100), 154(10), 116(26), 98(25), 69(7), 59(5).

Example 15h

Compound 15:

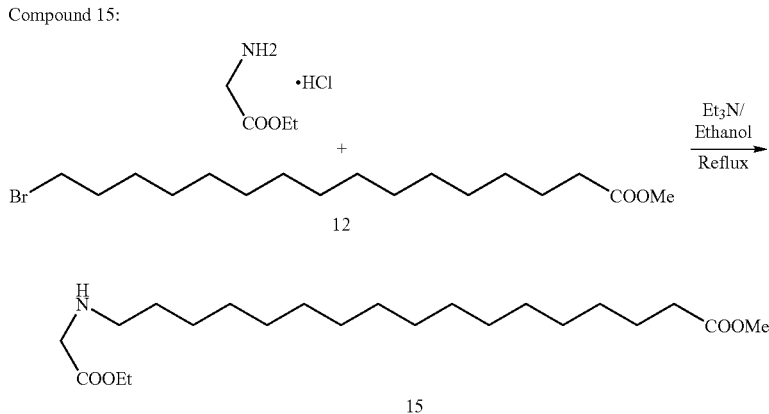

According to the general procedure (II), glycine ethyl ester hydrochloride (3.9 g, 28.6 mmol, 2 equiv), triethylamine (8 mL, 57.3 mmol, 4 equiv), and methyl 16-bromohexadecanoate (5 g, 14.3 mmol, 1 equiv) were mixed together in ethanol and reacted. Solvent was removed and the crude reaction mixture was purified through silica-gel column chromatography by using methanol/ethyl acetate (1:99) as the eluent to get the monoalkylated glycine ester (15). Yield 2.7 g (51%). $^1$H NMR (400 MHz, CDCl$_3$): δ 4.21-4.19 (m, 2H), 3.66 (s, 3H), 3.46-3.41 (m, 2H), 2.67 (m, 2H), 2.29 (t, J=7.6 Hz, 2H), 1.62-1.57 (m, 4H), 1.29-1.24 (m, 25H). $^{13}$C NMR (100 MHz, CDCl$_3$); δ 174.3, 172.2, 60.7, 51.4, 50.7, 49.5, 34.1, 29.8, 29.6, 29.5, 29.4, 29.2, 29.1, 27.2, 24.9, 14.2. EI/MS m/z (r.i.) 373(M+2, 9), 372(M+1, 44), 371(M+, 16), 325(16), 298(100), 266(16), 238(16), 224(9), 116(51), 74(9), 55(9).

Example 15i

Compound 58a:

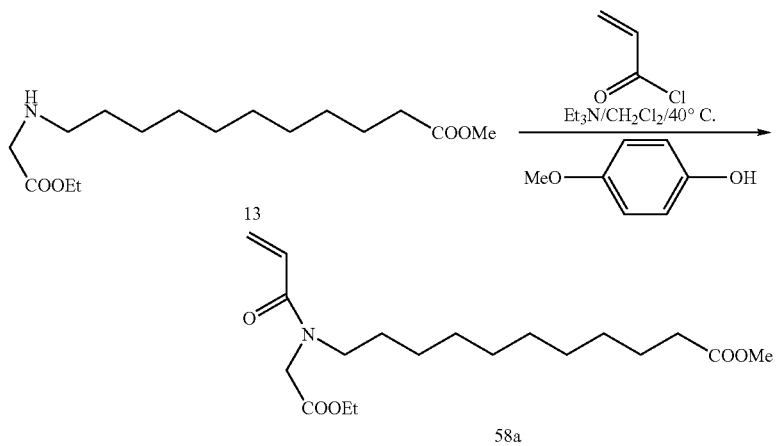

As mentioned in the general procedure (III), Compound 3 (12.4 g, 39.3 mmol, 1 equiv), triethylamine (7.1 mL, 51.1 mmol, 1.3 equiv), and small amount of p-methoxy phenol were mixed together in dry dichloromethane under argon atmosphere and the mixture was stirred at 40° C. Acryloyl chloride (3.8 mL, 47.2 mmol, 1.2 equiv) was added drop wise to the reaction mixture and the stirring was continued for 6 h. Then the crude acrylate monomer (58a) was purified through silica gel column chromatography with ethyl acetate/hexane (20:80) as the eluent. Yield 11.7 g (84%). $^1$H NMR (400 MHz, CDCl$_3$): δ 6.60-6.53 (m, 1H), 6.39-6.35 (m, 1H), 5.72-5.69 (m, 1H), 4.20-4.16 (m, 2H), 4.08-4.05 (m, 2H), 3.64 (s, 3H), 3.39-3.35 (m, 2H), 2.27 (t, J=7.2 Hz, 2H), 1.60-1.57 (m, 4H), 1.26-1.23 (m, 15H). $^{13}$C NMR (100 MHz, CDCl$_3$); δ 174.2, 169.2, 166.6, 128.7, 126.8, 61.6, 61.1, 51.4, 49.3, 48.3, 34.0, 29.4, 29.3, 29.2, 29.1, 29.0, 26.9, 26.7, 24.8, 14.1. EI/MS m/z (r.i.) 356(M+1, 3), 355(M+, 9), 324(20), 300(26), 282(67), 250(9), 228(100), 212(8), 170(21), 116(21), 98(9), 55(33).

Example 15j

Compound 58b:

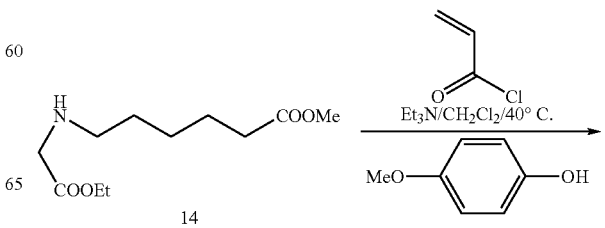

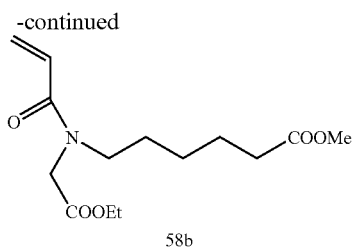

58b

As mentioned in the general procedure (III), Compound 14 (4.76 g, 20.6 mmol, 1 equiv), triethylamine (3.7 mL, 26.7 mmol, 1.3 equiv), and small amount of p-methoxy phenol were mixed together in dry dichloromethane under argon atmosphere and the mixture was stirred at 40° C. Acryloyl chloride (2.3 mL, 28.7 mmol, 1.4 equiv) was added drop wise to the reaction mixture and the stirring was continued for 6 h. Then the crude acrylate monomer (58b) was purified through silica gel column chromatography with ethyl acetate/hexane (25:75) as the eluent. Yield 4.83 g (82%). $^1$H NMR (400 MHz, $CDCl_3$): δ 6.57-6.50 (m, 1H), 6.36-6.28 (m, 1H), 5.70-5.64 (m, 1 μl), 4.19-4.11 (m, 2H), 4.05-4.03 (m, 2H), 3.63 (s, 3H), 3.41-3.34 (m, 2H), 2.27 (t, J=6.8 Hz, 2H), 1.64-1.49 (m, 4H), 1.33-1.20 (m, 5H). $^{13}$C NMR (100 MHz, $CDCl_3$); δ 173.9, 173.7, 169.1, 166.8, 166.6, 128.9, 128.3, 127.4, 126.7, 61.6, 61.1, 33.8, 33.6, 28.7, 27.0, 26.3, 26.1, 24.5, 24.4, 14.0. EI/MS m/Z (r.i.) 286(M+1, 5), 285(M+, 13), 254(10), 230 (24), 212(42), 200(14), 158(100), 116(25), 98(13), 69(9), 55(42).

Example 15k

Compound 58c:

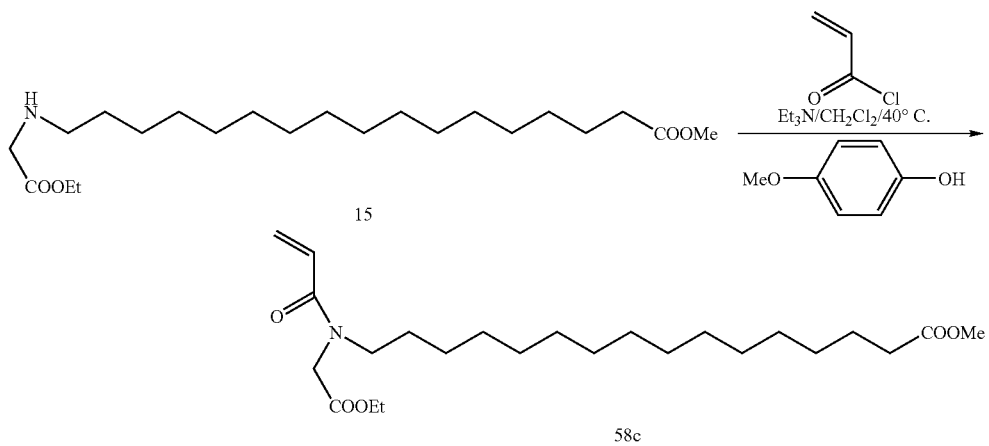

As mentioned in the general procedure (III), Compound 15 (2 g, 5.4 mmol, 1 equiv), triethylamine (1.0 mL, 7.0 mmol, 1.3 equiv), and small amount of p-methoxy phenol were mixed together in dry dichloromethane under argon atmosphere and the mixture was stirred at 40° C. Acryloyl chloride (0.6 mL, 7.5 mmol, 1.4 equiv) was added drop wise to the reaction mixture and the stirring was continued for 6 h. Then the crude acrylate monomer (58c) was purified through silica gel column chromatography with ethyl acetate/hexane (15:85) as the eluent. Yield 1.89 g (83%). $^1$H NMR (400 MHz, $CDCl_3$): δ 7.58-7.51 (m, 1H), 6.39-6.35 (m, 1H), 5.73-5.70 (m, 1H), 4.20-4.17 (m, 2H), 4.09-4.06 (m, 2H), 3.66 (S, 3H), 3.40-3.36 (m, 2H), 2.28 (t, J=7.6 Hz, 2H), 1.60-1.58 (m, 4H), 1.27-1.24 (m, 25H). $^{13}$C NMR (100 MHz, $CDCl_3$); δ 174.3, 169.3, 166.6, 128.8, 126.8, 61.6, 61.1, 51.4, 49.3, 48.3, 34.1, 29.6, 29.5, 29.4, 29.3, 29.2, 29.1, 26.9, 26.7, 24.9, 14.1. EI/MS m/z (r.i.) 426(M+1, 5), 425(M+, 13), 394(18), 371(26), 320(12), 298(100), 266(9), 212(12), 170(25), 116(22), 98(13), 55(31).

Example 15l

Procedure for Polymerization of 59a:

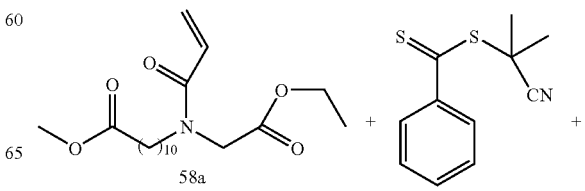

58a

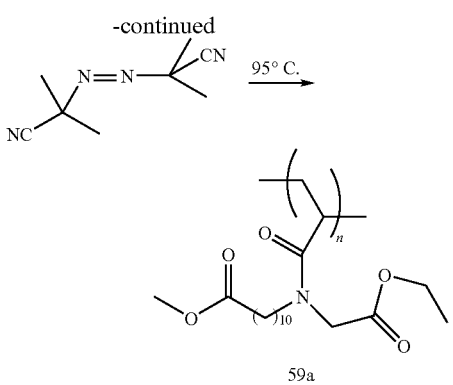

2,2'-Azobisisobutyronitrile (AIBN) (0.0008 g, 0.005 mmol), 2-cyanoisopropyl dithiobenzoate (CIDB), (0.003 g, 0.014 mmol), 58a (0.5 g, 1.408 mmol) were added to a dry Schlenk flask, flushed with nitrogen and degassed by freeze-pump-thaw cycles. The reaction mixture was kept at room temperature for 15 min, and it was transferred to a preheated oil bath at 95° C. and stirred for 15 min. Then the reaction mixture was dissolved in THF (2 mL), and precipitated in hexane and the precipitation was repeated thrice. Then the filtrate was decanted and the precipitate was vacuum dried. Yield 0.4 g, (80%), $M_n$—28,000, PDI—1.32. $^1$H-NMR (400 MHz, $CDCl_3$) δ 1.26 (bs, 17H), 1.598 (bs, 4), 2.26-2.30 (t, J=7.2, 2H), 2.65 (bs, 1H), 3.25 (bs, 2), 3.64 (s, 3H), 4.12 (bs, 4H).

Example 15m

Procedure for Polymerization of 59b:

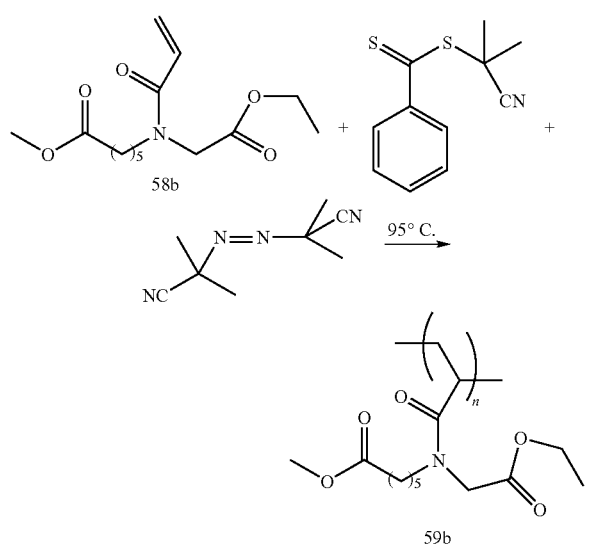

2,2'-Azobisisobutyronitrile (AIBN) (0.002 g, 0.012 mmol), 2-cyanoisopropyl dithiobenzoate, (0.008 g, 0.036 mmol), 59b (1 g, 3.5 mmol) were added to a dry Schlenk flask, flushed with nitrogen and degassed by freeze-pump-thaw cycles The reaction mixture was kept at room temperature for 15 min, and it was transferred to a preheated oil bath at 95° C. and stirred for 45 min. Then the reaction mixture was dissolved in THF (3 mL), and precipitated in hexane. This pre- cipitation was repeated thrice, then the precipitate was collected and vacuum dried. Yield 0.93 g, (93%), $M_n$—24,100, PDI—1.30. $^1$H-NMR (400 MHz, $CDCl_3$) δ 1.23 (bs, 7H), 1.60 (bs, 4H), 2.28 (bs, 2H), 2.57 (bs, 1H), δ 3.24 (bs, 2H), 3.66 (s, 3H), 4.09 (bs, 4H).

Example 15n

Procedure for Polymerization of 59c:

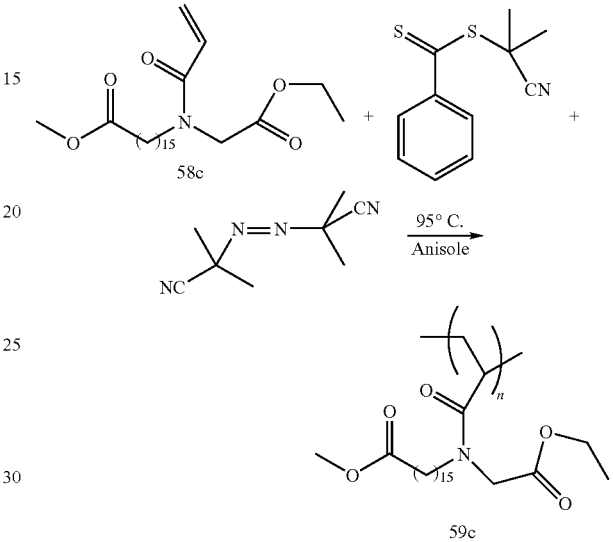

2,2'-Azobisisobutyronitrile (AIBN) (0.001 g, 0.006 mmol), 2-cyanoisopropyl dithiobenzoate (CIDB), (0.004 g, 0.018 mmol), 59c (1 g, 2.35 mmol) anhydrous anisole (0.4 mL) were added to a dry Schlenk flask, flushed with nitrogen and degassed by freeze-pump-thaw cycles. The reaction mixture was kept at room temperature for 15 minutes, and it was transferred to a preheated oil bath at 95° C. and stirred for 45 min. Then the reaction mixture was dissolved in THF (3 mL), and precipitated in hexane. The precipitation was repeated thrice and then the precipitate was collected and vacuum dried. Yield 0.90 g, (90%), $M_n$—30,000, PDI—1.36. $^1$H-NMR (400 MHz, $CDCl_3$) δ 1.24 (bs, 27H), 1.60 (m, 4H), 2.27-2.30 (t, J=7.6, 2H), 2.64 (bs, 1 µl), 3.25 (bs, 2H), δ 3.65 (s, 3H), 4.12 (bs, 4H).

Example 15o

General Procedure for Hydrolysis:

The polymer (1 equiv) dissolved in methanol was taken in a single neck round bottom flask, potassium hydroxide (5 equiv) was added and stirred at room temperature for 36 h under argon atmosphere. Methanol was removed under reduced pressure, the residue was dissolved in water and neutralized with 3M HCl. The precipitate was filtered and dried under vacuum. The polymers were characterized by using $H^1$ NMR spectroscopy.

Compound 60a: $^1$H-NMR (400 MHz, MeOD): δ 1.37 (bs, 14H), 1.64 (bs, 4H), 2.30-2.34 (t, J=6.4, 2H), 2.68 (bs, 1H), 3.29 (bs, 2H), 4.05 (bs, 2H).

Compound 60b: $^1$H-NMR (400 MHz, MeOD): δ 1.38 (bs, 2H), 1.68 (bs, 6H), 2.36 (bs, 2H), 2.82 (bs, 1H), 3.42 (bs, 2H), 4.06 (bs, 2H).

Compound 60c: ¹H-NMR (400 MHz, MeOD): δ 1.35 (bs, 24H), 1.64 (bs, 4), 2.30-2.33 (t, J=7.2, 2H), 2.81 (bs, 1H), 3.27 (bs, 2H), 4.11 (bs, 2H).

Example 16

TEM measurements were performed on polymers 60a-c using a JEOL 100CX 100 KV TEM. To prepare the solutions for doing TEM for the vesicle-like structures the polymers were dissolved in appropriate amount of water with LiOH/CsOH as the base. For each COOH unit present in the polymer 2 equiv of LiOH/CsOH were added in order to form the carboxylate salts. This solution was then sonicated for 2 h to ensure the solubility in water. To prepare the solutions for doing TEM for inverted micelle-like assemblies, an appropriate amount of polymer was taken with calculated amount of toluene. To make the polymer soluble in toluene 1 equiv of CsOH was added to the polymer solution along with 4 equiv of water for each carboxylic acid group present in the measured amount of polymer. This solution was then sonicated for 4 h to get the homogeneous solution. Samples were prepared by dipping copper EM grids (pre-coated with the thin film of Formvar and then coated with carbon) in aqueous or toluene solutions of the polymers and dried at room temperature.

Example 17

Dynamic Light Scattering (DLS) and Static Light Scattering (SLS) Experiments:

Dynamic light scattering experiments were performed on polymers 60a-c by using a digital correlator and goniometer. The light source was solid-state laser system, operating at 514 nm. The temperature was kept constant at 25° C. throughout the experiment. Dust was eliminated by filtering the solution through 0.22 μm filter. All the measurements were done at a correlation time of 1 min. The particle size was analyzed using CONTIN program.

For SLS the polymer was taken in three different concentrations and detected at different angle from 35 to 135° and measurements acquired during 30 seconds at every angle. Finally from the slope extrapolated to data at zero concentration, the radius of gyration (RG) was calculated using Zimm plot.

Example 18

The UV-Vis absorption spectra of polymeric systems of 60a-c were recorded on a spectrophotometer using quartz cells. Fluorescence spectra were recorded on a fluorimeter. The spectra were recorded using a quartz cuvette. The polymer solution was made in a similar way to TEM, to the clear solution rhodamine 6G was added and sonicated for 2 h. The solution was then filtered through 0.2 μm filter and analyzed.

FIG. 5 shows the fluorescence quenching of the dye rhodamine 6G, in presence of the inverted micelle, which proves that the dye is confined in a small space.

Example 19

With reference to FIG. 4, various N-alkyl amphiphilic monomers can be prepared, as follows for subsequent polymerization and assembly. Reference numbers 100-103 refer only to this example.

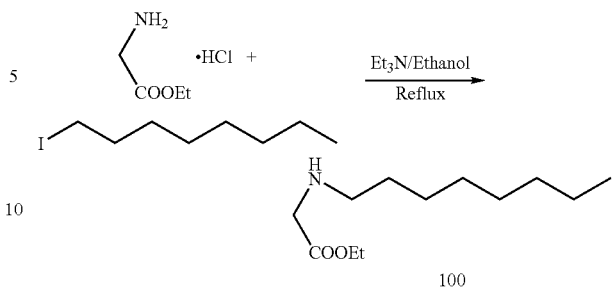

Example 19a

1-Iodooctane (40 g, 0.166 mol, 1 equiv), glycmethylester hydrochloride (46.5 g, 0.333 mol, 2 equiv) and triethylamine (92.8 mL, 0.666 mol, 4 equiv) were mixed up in ethanol (400 mL) and the reaction mixture was refluxed for 24 h under argon atmosphere. After the solvent removal, the residue was dissolved in water and extracted by using dichloromethane. Solvent was removed and the crude reaction mixture was subjected to silica gel column chromatography by using ethyl acetate (100%) as the eluent to get the monoalkylated glycine ester (100). Yield (16.5 g, 46%). ¹H NMR: δ 4.20 (q, J=7.2 Hz, 2H), 3.37 (s, 2H), 3.17 (t, J=7.2 Hz, 2H), 1.86 (s, 1H), 1.46 (quin, J=7.2 Hz, 2H), 1.27-1.23 (m, 13H), 0.84 (t, J=7.2 Hz, 3H).

Example 19b

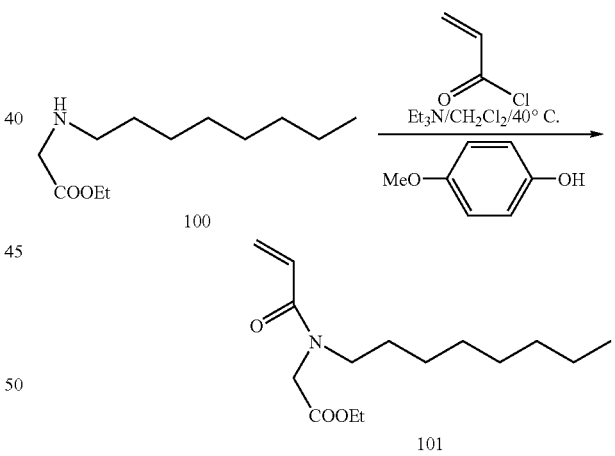

Compound (100) (5.75 g, 0.027 mol, 1 equiv), Et₃N (4.5 mL, 0.032 mol, 1.2 equiv), and small amount of p-methoxy phenol (10 mg) were mixed together in dry dichloromethane under argon atmosphere and the mixture was stirred at 40° C. Acrolyl chloride (2.8 mL, 0.035 mol, 1.3 equiv) was added dropwise to the reaction mixture and the stirring was continued for 6 h. Then the crude reaction mixture was washed with 1N HCl, saturated NaHCO₃ and brine solution. Solvent was removed from the reaction mixture, and the acrylate monomer (101) was purified through silica gel column chromatography with ethyl acetate/hexane (25:75) as the eluent. Yield (6.6 g, 92%). ¹H NMR: δ 7.13-7.08 (m, 1H), 6.44 (dd, J=16.8 Hz, 2 Hz, 1H), 5.83 (dd, J=10.4 Hz, 2 Hz, 1H), 4.38 (q, J=7.2

Hz, 2H), 4.07 (s, 2H), 3.39 (t, J=7.6 Hz, 2H), 1.53 (quin, J=7.2 Hz, 2H), 1.26-1.23 (m, 13H), 0.84 (t, J=7.2 Hz, 3H).

Example 19c

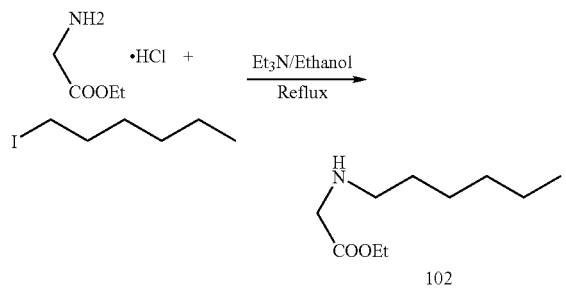

1-Iodohexane (16 g, 0.075 mol, 1 equiv), glycmethylester hydrochloride (19.0 g, 0.151 mol, 2 equiv) and triethylamine (42.0 mL, 0.302 mol, 4 equiv) were mixed up in ethanol (200 mL) and the reaction mixture was refluxed for 24 h under argon atmosphere. After the solvent removal, the residue was dissolved in water and extracted by using dichloromethane. Solvent was removed and the crude reaction mixture was subjected to silica gel column chromatography by using ethyl acetate (100%) as the eluent to get the monoalkylated glycine ester (102). Yield (6.9 g, 49%). $^1$H NMR: δ 4.18 (q, J=6.4 Hz, 2H), 3.4 (s, 2H), 3.21 (t, J=6.8 Hz, 2H), 1.81 (s, 1H), 1.41 (quin, J=6.8 Hz, 2H), 1.30-1.24 (m, 9H), 0.88 (t, J=6.8 Hz, 3H).

Example 19d

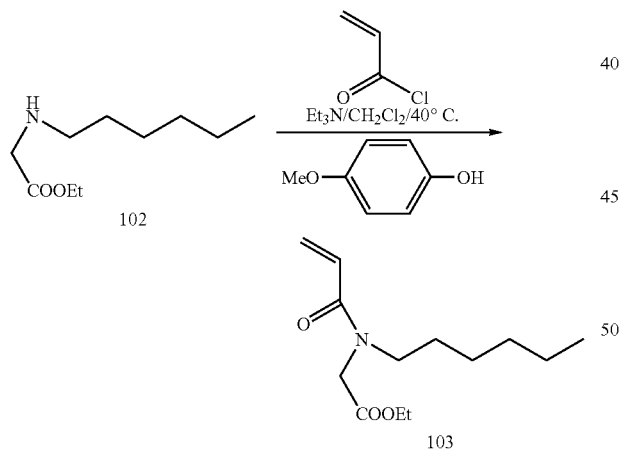

Compound (102) (4.0 g, 0.021 mol, 1 equiv), Et$_3$N (3.9 mL, 0.028 mol, 1.3 equiv), and small amount of p-methoxy phenol (10 mg) were mixed together in dry dichloromethane under argon atmosphere and the mixture was stirred at 40° C. Acrolyl chloride (2.28 mL, 0.028 mol, 1.3 equiv) was added dropwise to the reaction mixture and the stirring was continued for 6 h. Then the crude reaction mixture was washed with 1N HCl, saturated NaHCO$_3$ and brine solution. Solvent was removed from the reaction mixture, and the acrylate monomer (103) was purified through silica gel column chromatography with ethyl acetate/hexane (25:75) as the eluent. Yield (4.8 g, 93%). $^1$H NMR: δ 7.10-7.06 (m, 1H), 6.48 (dd, J=16.4 Hz, 2.4 Hz, 1H), 5.86 (dd, J=10.2 Hz, 2.4 Hz, 1H), 4.32 (q, J=6.8 Hz, 2H), 4.02 (s, 2H), 3.37 (t, J=6.8 Hz, 2H), 1.58 (quin, J=6.8 Hz, 2H), 1.31-1.26 (m, 9H), 0.86 (t, J=6.8 Hz, 3H).

Example 20

As a variation on the amphiphiles of FIG. 1, a hydrophilic component can comprise a poly(alkylene oxide), e.g., of ethylene oxide, as shown below, with the reference numbers germane only to the compounds of this example.

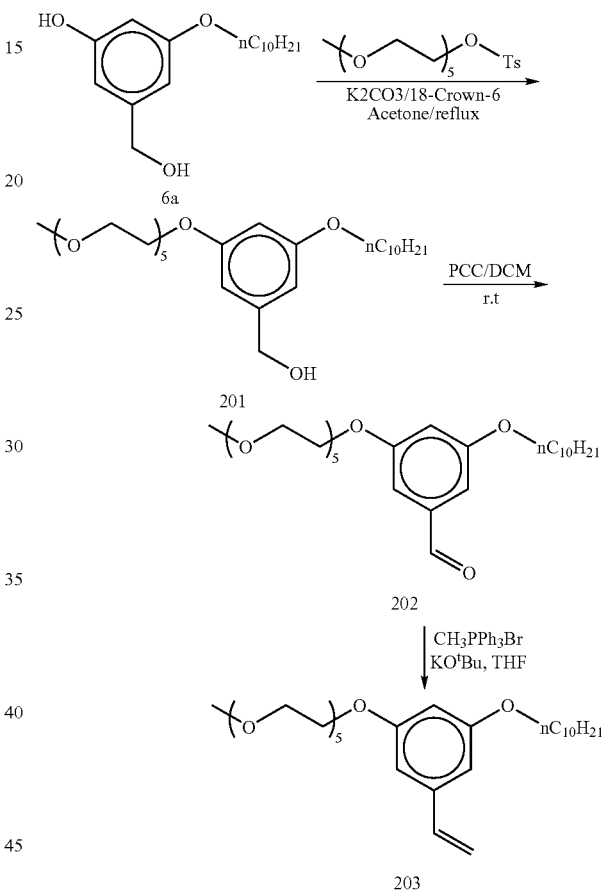

Example 20a

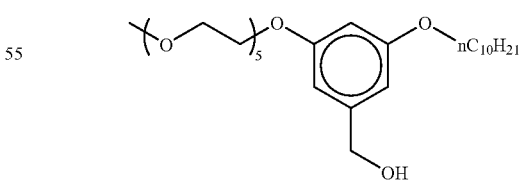

Compound 6a (12 g, 42.8 mmol, 1 equiv), potassium carbonate (8.9 g, 64.2 mmol, 1.5 equiv), 18-Crown-6 (1.2 g, 4.28 mmol, 0.1 equiv) and the tosylate of pentaethylene glycol mono methylether (17.4 g, 38.6 mmol, 0.9 equiv) were mixed together in acetone and refluxed overnight. Upon completion of reaction, solvent was removed and the crude reaction mixture was dissolved in water and extracted with ethyl acetate. The crude product was purified through silica gel column chromatography by using ethyl acetate (100%) as an eluent. Yield 19.1 g (96%). $^1$H NMR (400 MHz, CDCl$_3$): δ 6.51 (d, J=9.6 Hz, 2H), 6.39 (t, J=2.4 Hz, 1H), 4.59 (s, 2H), 4.1 (t, J=4.8 Hz, 2H), 3.91 (t, J=6.4 Hz, 2H), 3.82 (t, J=4.8 Hz, 2H), 3.72-3.60 (m, 16H), 3.37 (s, 3H), 1.78-1.69 (quin, J=6.4 Hz, 2H), 1.44-1.21 (m, 14H), 0.87 (t, J=6.4 Hz, 3H). $^{13}$C NMR (100 MHz, CDCl$_3$): δ 160.1, 159.7, 143.5, 105.1, 104.6, 100.2, 71.6, 70.5, 70.3, 70.2, 70.1, 69.4, 67.7, 67.1, 64.6, 58.7, 31.6, 29.3, 29.2, 29.1, 29.0, 28.9, 25.8, 22.4, 13.8. EI/MS m/z (r.i.) 517 (M+3, 23), 515 (M+1, 14), 514 (M+, 45), 412 (5), 350 (5), 324 (7), 280 (38), 249 (5), 199 (8), 140 (40), 103 (24), 59 (100).

Example 20b

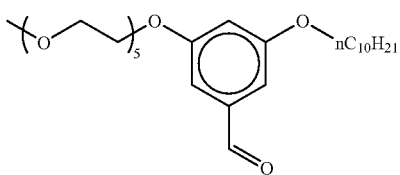

To a stirred solution of compound 201 (9.2 g, 17.8 mmol, 1 equiv) in dichloromethane (100 mL) was added pyridinium chlorochromate (5.0 g, 23.2 mmol, 1.3 equiv). The mixture was stirred at room temperature for 4 h. The reaction mixture was filtered over alumina and the filtrate was evaporated and purified by silica gel column chromatography to afford 8.3 g of corresponding aldehyde (Yield 91%). $^1$H NMR (400 MHz, CDCl$_3$): δ 9.85 (s, 1H), 6.97 (m, 2H), 6.70 (d, J=1.2 Hz, 1H), 4.13 (t, J=4.4 Hz, 2H), 3.94 (t, J=6.4 Hz, 2H), 3.84 (t, J=4.4 Hz, 2H), 3.71-3.60 (m, 16H), 3.34 (m, 3H), 1.65 (quin, J=6.8 Hz, 2H), 1.42-1.11 (m, 14H), 0.85 (t, J=6.8 Hz, 3H). $^{13}$C NMR (100 MHz, CDCl$_3$): δ 191.8, 160.6, 160.3, 138.2, 108.0, 107.9, 107.4, 71.8, 70.7, 70.52, 70.50, 70.48, 70.46, 70.4, 69.5, 68.3, 67.7, 58.9, 31.8, 29.5, 29.4, 29.3, 29.2, 29.0, 25.9, 22.6, 14.0.

Example 20c

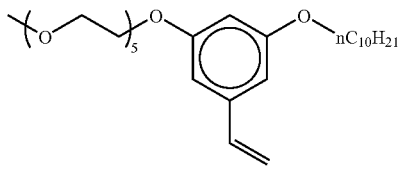

Commercially available CH$_3$PPh$_3$Br (6.4 g, 17.7 mmol, 1.3 equiv) was taken in dry THF (75 mL) and KO$^t$BU (1.95 g, 17.7 mmol, 1.3 equiv) was added to this under argon atmosphere. This reaction mixture was stirred for 20 min and a solution of aldehyde (7 g, 13.7 mmol, 1 equiv) in 75 mL of dry THF) was added slowly with syringe to the above solution. The reaction mixture was further stirred at room temperature for 4 h. The reaction mixture was filtered and the filtrate evaporated and purified by silica gel chromatography to afford 5.9 g of compound 203 (Yield 85%). $^1$H NMR (400 MHz, CDCl$_3$): δ 6.55-6.45 (m, 3H), 6.29 (t, J=2.8 Hz, 1H), 5.62 (d, J=23.6 Hz, 1H), 5.11 (d, J=14.4 Hz, 1H), 3.99 (t, J=6.8 Hz, 2H), 3.81 (t, J=8.4 Hz, 2H), 3.73-3.39 (m, 18H), 3.25 (s, 3H), 1.65 (quin, J=8.8 Hz, 2H), 1.34-1.11 (m, 14H), 0.79 (t, J=8.8 Hz, 3H). $^{13}$C NMR (100 MHz, CDCl$_3$): δ 159.9, 159.6, 138.9, 136.5, 113.6, 104.7, 104.3, 100.6, 71.5, 70.3, 70.2, 70.1, 70.0, 69.3, 67.5, 66.9, 58.5, 31.5, 29.2, 29.0, 28.9, 28.8, 25.6, 22.3, 14.0.

Example 21a

Acrylamide polymers of this invention, e.g., N-alkyl substituted, can be prepared as follows. Again, numerical references apply only to the compounds of example 19.

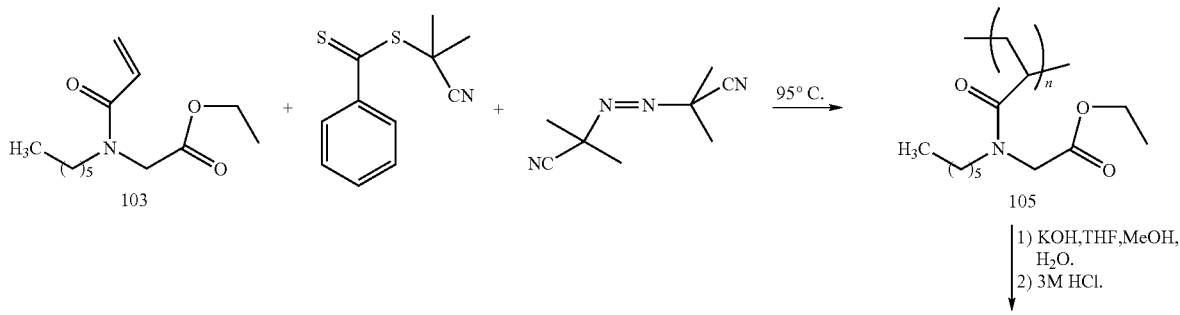

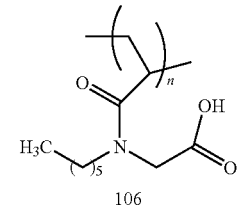

2,2'-Azobisisobutyronitrile (AIBN) (0.001 g, 0.006 mmol), 2-cyanoisopropyl dithiobenzoate, 0.004 g (0.017 mmol), monomer (103) 0.5 g (2.1 mmol) were added to a dry Schlenk flask, flushed with nitrogen and degassed by freeze-pump-thaw cycles The reaction mixture was kept at room temperature for 15 min, and it was transferred to a preheated oil bath at 95° C. and stirred for 45 min. Then the reaction mixture was dissolved in THF (3 mL), and precipitated in methanol. This precipitation was repeated thrice, and then the precipitate was collected and vacuum dried. Yield 90%, $M_n$—23,000, PDI—1.36. Then 1 g of potassium hydroxide was added to the polymer (105) in THF, methanol and water mixture (6 ml: 3 ml: 1 ml), heated in round bottom flask at 60° C. for 20 hrs, and evaporated the solvents and 10 ml of water was then added. This solution was heated at 60° C. for 12 hrs, and then the reaction mixture was cooled to RT, and then neutralized with 3 M HCl solution to precipitate the polymer. The polymer was filtered and vacuum dried. $^1$H-NMR (400 MHz, DCON(CD$_3$)) δ 0.87 (s, 3H), 1.25 (m, 10H), 2.50 (bs, 1H), 3.40 (bs, 2H), δ 4.15 (bs, 2H).

Example 21b

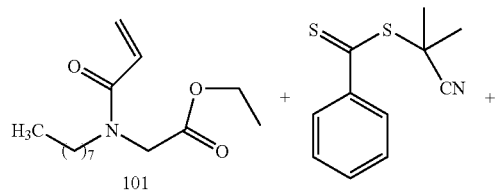

-continued

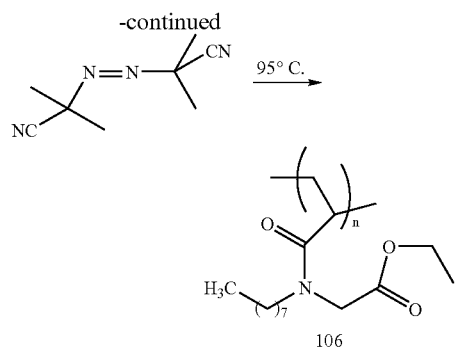

2,2'-Azobisisobutyronitrile (AIBN) (0.001 g, 0.006 mmol), 2-cyanoisopropyl dithiobenzoate, 0.005 g (0.023 mmol), monomer 101 1 g (3.7 mmol) were added to a dry Schlenk flask, flushed with nitrogen and degassed by freeze-pump-thaw cycles The reaction mixture was kept at room temperature for 15 min, and it was transferred to a preheated oil bath at 95° C. and stirred for 45 min. Then the reaction mixture was dissolved in TBF (3 mL), and precipitated in methanol. This precipitation was repeated thrice, and then the precipitate was collected and vacuum dried. Yield 70%, $M_n$—23,000, PDI—1.18. $^1$H-NMR (400 MHz, CDCl$_3$) δ 0.87 (s, 3H), 1.25 (m, 171), 2.65 (bs, 1H), 3.25 (bs, 2H), 4.18 (bs, 4H)

Example 22a

As a further variation, consider carboxylate terminated poly(ethylene oxide) hydrophilic components, in conjunction with a representative amphiphile monomer and corresponding polymer.

Synthesis of OEG Based Carboxylate Monomer:

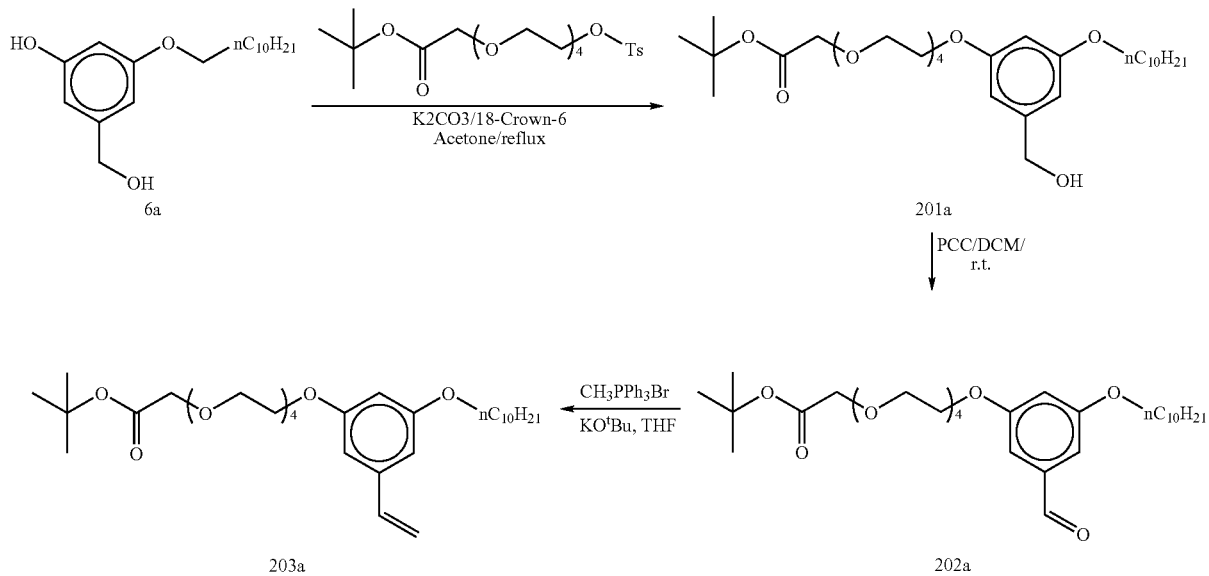

Compound 201a:

$^1$H NMR (400 MHz, CDCl$_3$): δ6.51 (d, J=6 Hz, 2H), 6.39 (t, J=2.0 Hz, 1H), 4.60 (s, 2H), 4.11 (t, J=4.4 Hz, 2H), 4.01 (d, J=4.4 Hz, 2H), 3.91 (t, J=6.4 Hz, 2H), 3.83 (t, J=5.2 Hz, 2H), 3.71-3.65 (m, 14H), 1.76 (quin, J=6.8 Hz, 2H), 1.47-1.21 (m, 23H), 0.87 (t, J=6.8 Hz, 3H).

Compound 202a:

$^1$H NMR (400 MHz, CDCl$_3$): δ 9.88 (s, 1H), 6.99 (m, 2H), 6.72 (d, J=1.2 Hz, 1H), 4.15 (t, J=4.8 Hz, 2H), 4.0 (s, 2H), 3.97 (t, J=6.4 Hz, 2H), 3.86 (t, J=4.8 Hz, 2H), 3.72-3.66 (m, 12H), 1.77 (quin, J=6.8 Hz, 2H), 1.46 (s, 9H), 1.38-1.27 (m, 14H), 0.87 (t, J=6.8 Hz, 3H).

Compound 203a:

$^1$H NMR (400 MHz, CDCl$_3$): δ 6.61-6.56 (m, 3H), 6.39 (t, J=2.0 Hz, 1H), 5.70 (d, J=17.6 Hz, 1H), 5.22 (d, J=10.8 Hz, 1H), 4.12 (t, J=4.4 Hz, 2H), 4.01 (s, 2H), 3.92 (t, J=6.8 Hz, 2H), 3.84 (t, J=4.8 Hz, 2H), 3.72-3.66 (m, 12H), 1.76 (quin, J=6.8 Hz, 2H), 1.47 (s, 91H), 1.38-1.24 (m, 14H), 0.88 (t, J=6.4 Hz, 3H).

2,2'-Azobisisobutyronitrile (AIBN) (0.0004 g, 0.002 mmol), 2-cyanoisopropyl dithiobenzoate, 0.002 g (0.009 mmol), monomer (203a) 0.5 g (0.88 mmol) were added to a dry Schlenk flask, flushed with nitrogen and degassed by freeze-pump-thaw cycles The reaction mixture was kept at room temperature for 15 min, and it was transferred to a preheated oil bath at 95° C. and stirred for 45 min. Then the reaction mixture was dissolved in THF (3 mL), and precipitated in methanol. This precipitation was repeated thrice, and then the precipitate was collected and vacuum dried. Yield 80%, M$_n$—26,000, PDI—1.12. Then 1 g of potassium hydroxide was added to the polymer (204a) in TBE, methanol and water mixture (6 ml: 3 ml: 1 ml), heated in round bottom flask at 60° C. for 20 hrs, and evaporated the solvents and 10 ml of water was then added. This solution was heated at 90° C. for 12 hrs, and then the reaction mixture was cooled to RT, and then neutralized with 3 M HCl solution to precipitate the polymer. The polymer (205a) was filtered and vacuum dried. $^1$H-NMR (400 MHz, MeOD) δ 0.92 (s, 3H), δ 1.32 (s, 16H), 1.72 (s, 3H), 3.59 (bs, 14H), 3.74 (bs, 4H), 5.82 (s, 2H) 6.3 (s, 1H).

Example 20d

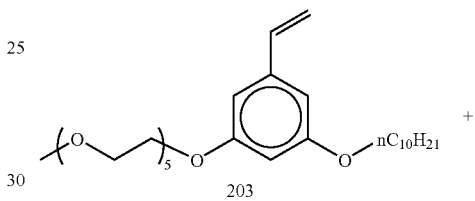

Example 22b

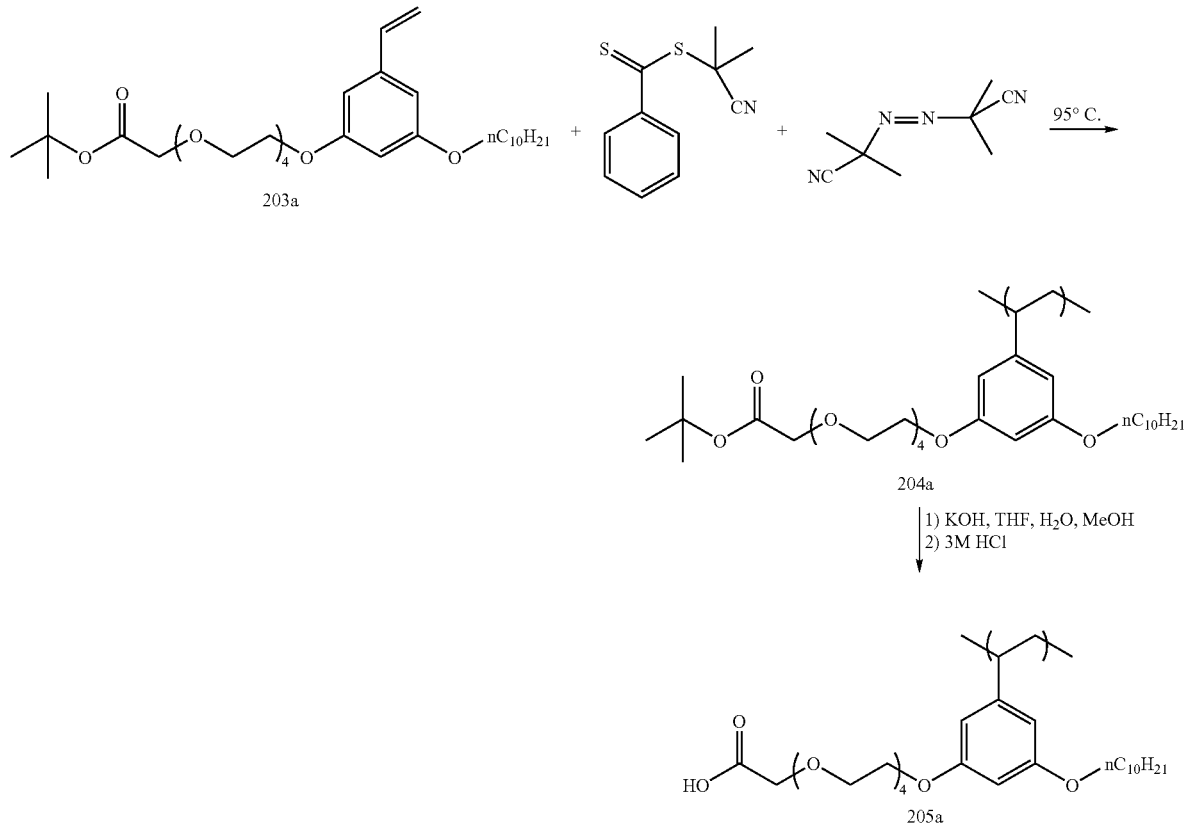

-continued

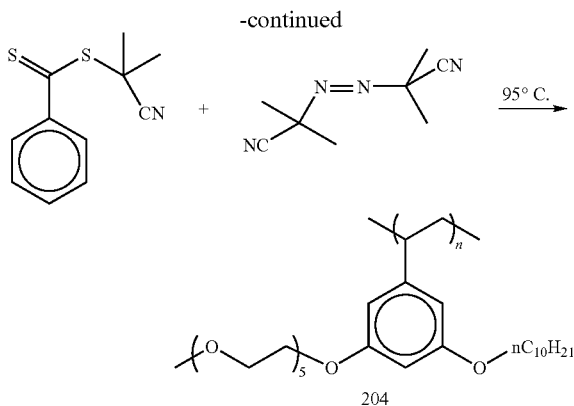

204

2,2'-Azobisisobutyronitrile (AIBN) (0.0004 g, 0.0024 mmol), 2-cyanoisopropyl dithiobenzoate (CIDB), (0.003 g, 0.014 mmol), 203 (0.51 g, 1.0 mmol) were added to a dry Schlenk flask, flushed with nitrogen and degassed by freeze-pump-thaw cycles. The reaction mixture was kept at room temperature for 15 minutes, and transferred the reaction flask to oil bath, which was preheated at 95° C. and stirred for 15 minutes. Then the reaction mixture was dissolved in THF (2 mL), and precipitated in hexane and the precipitation was repeated twice. The filtrate was decanted and the precipitate (kind of gel) was vacuum dried. Yield 0.4 g, 78%, $M_n$—11,000, PDI—1.1. $^1$H NMR (400 MHz, $CDCl_3$): δ 6.32-6.38 (m, 3H), 3.72-3.54 (m, 22H), 3.36 (s, 1H), 1.82-1.80 (m, 3H), 1.62-1.20 (m, 16H), 0.88 (t, J=6.4 Hz, 3H).

As demonstrated, a new class of amphiphilic polymers containing both hydrophilic and lipophilic functionalities in each repeats unit has been synthesized. These polymers (monomeric units >1, above) are soluble in both aqueous and organic solvents, where they assemble into micelle-like or inverse micelle-like structures. Amphiphilic functions reported here are likely to form the basis for new nanoscale assemblies in solution and in solid state, which could have implications in a broad range of applications. The change in assembly surface appears to be the amplified consequence of change in molecular-level confirmation within each monomeric unit. Polymers with such properties can find use in applications such as carriers for drug delivery through lipid bilayers and as components of smart adhesives.

I claim:

1. An amphiphilic polymer compound comprising a polymeric component of a formula

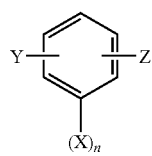

wherein X is selected from alkenyl and substituted alkenyl moieties, and n is an integer greater than 1; and Y and Z independently comprise and are independently selected from oxyacetic acid, substituted oxyacetic acid, oxyacetic acid salt, substituted oxyacetic acid salt, oxyacetic acid ester, oxyacetamide, substituted oxyacetamide, poly (ethylene oxide), substituted poly (ethylene oxide), benzoxy, substituted benzoxy, alkoxy and substituted alkoxy moieties, one of said Y and Z a hydrophilic moiety and one of said Y and Z a hydrophobic moiety, said Y and Z moieties together providing amphiphilic character to said polymer, said polymer having amphiphilic character sufficient for assembly of a micellar configuration in one of a polar and a non-polar medium and inversion of said micellar configuration with change in medium polarity.

2. The compound of claim 1 wherein Y is an oxyacetate moiety and Z is selected from alkoxy, substituted alkoxy, benzoxy and substituted benzoxy moieties.

3. The compound of claim 2 wherein Z is selected from an alkoxy moiety ranging from about $C_2$ to about $C_{20}$, and a benzoxy moiety.

4. The compound of claim 1 wherein Y comprises a poly (ethylene oxide) moiety terminated with a component selected from H, alkyl, oxyacetate, alkoxycarbonyl and alkylcarbonyl; and Z is selected from alkoxy, substituted alkoxy, benzoxy and substituted benzoxy moieties.

5. The compound of claim 1 homopolymeric.

6. An amphiphilic polymer compound comprising a polymeric component of a formula

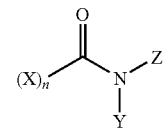

wherein X is selected from alkenyl and substituted alkenyl moieties, and n is an integer greater than 1; and Y and Z independently comprise and are independently selected from H, alkyl, substituted alkyl, ethanoic acid, substituted ethanoic acid, an ethanoic acid salt, a substituted ethanoic acid salt, ethanoic acid ester, a substituted ethanoic acid ester, ethanoic acid amide, and N-substituted ethanoic acid amide moieties, one of said Y and Z a hydrophilic moiety and one of said Y and Z a hydrophobic moiety, said Y and Z together providing amphiphilic character to said polymer, said polymer having amphiphilic character sufficient for assembly of a micellar configuration in one of a polar and a non-polar medium and inversion of said micellar configuration with change in medium polarity.

7. The compound of claim 6 wherein Y is selected from ethanoic acid salts and substituted ethanoic acid salts, and Z is selected from H, alkyl and substituted alkyl moieties.

8. The compound of claim 7 wherein Y is an ethanoic acid salt and Z is selected from alkyl and carboxy-substituted alkyl moieties.

9. The compound of claim 6 wherein Y is a substituted ethanoic acid salt and Z is H.

10. The compound of claim 9 wherein said substituent is selected from alkyl, substituted alkyl, benzyl and substituted benzyl groups.

11. The compound of claim 6 homopolymeric.

12. The compound comprising a polymeric component of a formula

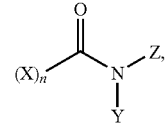

copolymeric and comprising a component of a polymer of claim 1.

13. A composition comprising:
an amphiphilic polymer selected from a compound comprising a polymeric component of a formula

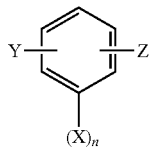

wherein X is selected from alkenyl and substituted alkenyl moieties, and n is an integer greater than 1; and Y and Z independently comprise and are independently selected from oxyacetic acid, substituted oxyacetic acid, oxyacetic acid salt, substituted oxyacetic acid salt, oxyacetic acid ester, oxyacetamide, substituted oxyacetamide, poly (ethylene oxide), substituted poly (ethylene oxide), benzoxy, substituted benzoxy, alkoxy and substituted alkoxy moieties, one of said Y and Z a hydrophilic moiety and one of said Y and Z a hydrophobic moiety, said Y and Z moieties together providing amphiphilic character to said polymer, said polymer having amphiphilic character sufficient for assembly of a micellar configuration in one of a polar and a non-polar medium and inversion of said micellar configuration with change in medium polarity; and a compound comprising a polymeric component of a formula

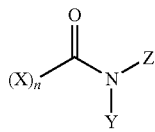

wherein X is selected from alkenyl and substituted alkenyl moieties, and n is an integer greater than 1; and Y and Z independently comprise and are independently selected from H, alkyl, substituted alkyl, ethanoic acid, substituted ethanoic acid, an ethanoic acid salt, a substituted ethanoic acid salt, ethanoic acid ester, a substituted ethanoic acid ester, ethanoic acid amide, and N-substituted ethanoic acid amide moieties, one of said Y and Z a hydrophilic moiety and one of said Y and Z a hydrophobic moiety, said Y and Z together providing amphiphilic character to said polymer, said polymer having amphiphilic character sufficient for assembly of a micellar configuration in one of a polar and a non-polar medium and inversion of said micellar configuration with change in medium polarity; and
a fluid medium comprising at least one of a first fluid and a second fluid, one said fluid polar and the other said fluid non-polar, said polymer in a micellar configuration responsive to said medium.

14. The composition of claim 13 comprising a medium of a first fluid and a component at least partial insoluble therein, said polymeric micelle configured about said component.

15. The composition of claim 14 comprising said second fluid, said component at least partially soluble in said second fluid.

16. The composition of claim 13 wherein said amphiphilic polymer comprises a polymer comprising a polymeric component of a formula

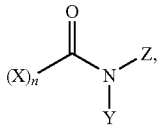

wherein Y is selected from ethanoic acid salts and substituted ethanoic acid salts, and Z is selected from H, alkyl and substituted alkyl moieties.

17. The composition of claim 13 wherein said amphiphilic polymer comprises a polymer comprising a polymeric component of a formula

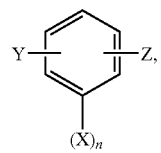

wherein Y is an oxyacetate moiety and Z is selected from alkoxy, substituted alkoxy, benzoxy and substituted benzoxy moieties.

18. The composition of claim 13 wherein said amphiphilic polymer is copolymeric, comprising an acrylate block component of a polymer comprising a polymeric component of a formula

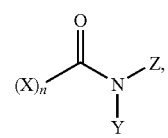

said copolymer biodegradable.

19. A method of using an amphiphilic polymer structure for change of micellar configuration, said method comprising:
providing a polymer selected from a compound comprising a polymeric component of a formula

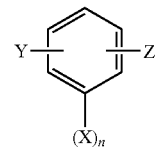

wherein X is selected from alkenyl and substituted alkenyl moieties, and n is an integer greater than 1; and Y and Z independently comprise and are independently selected from oxyacetic acid, substituted oxyacetic acid, oxyacetic acid salt, substituted oxyacetic acid salt, oxyacetic acid ester, oxyacetamide, substituted oxyacetamide, poly(ethylene oxide), substituted poly(ethylene oxide), benzoxy, substituted benzoxy, alkoxy and substituted alkoxy moieties, one of said Y and Z a hydrophilic moiety and one of said Y and Z a hydrophobic moiety, said Y and Z moieties together providing amphiphilic character to said polymer, said polymer having amphiphilic character sufficient for assembly of a micellar configuration in one of a polar and a non-polar medium and inversion of said micellar configuration with change in medium polarity; and a compound comprising a polymeric component of a formula

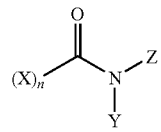

wherein X is selected from alkenyl and substituted alkenyl moieties, and n is an integer greater than 1; and Y and Z independently comprise and are independently selected from H, alkyl, substituted alkyl, ethanoic acid, substituted ethanoic acid, an ethanoic acid salt, a substituted ethanoic acid salt, ethanoic acid ester, a substituted ethanoic acid ester, ethanoic acid amide, and N-substituted ethanoic acid amide moieties, one of said Y and Z a hydrophilic moiety and one of said Y and Z a hydrophobic moiety, said Y and Z together providing amphiphilic character to said polymer, said polymer having amphiphilic character sufficient for assembly of a micellar configuration in one of a polar and a non-polar medium and inversion of said micellar configuration with change in medium polarity; and introducing said polymer to at least one of a polar medium to assemble one micellar configuration, and a non-polar medium to assemble another micellar configuration.

20. The method of claim 19 wherein one of said media comprises a component at least partially insoluble therein, said polymer configured about said component.

21. The method of claim 20 wherein contact with said other medium inverts said polymer configuration.

* * * * *